United States Patent
Matsuda et al.

(10) Patent No.: US 7,479,574 B2
(45) Date of Patent: Jan. 20, 2009

(54) METHOD OF PRODUCING MACROCYCLIC KETONE, AND INTERMEDIATE THEREOF

(75) Inventors: Hiroyuki Matsuda, Kanagawa (JP);
Shigeru Tanaka, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 11/667,476

(22) PCT Filed: Nov. 11, 2004

(86) PCT No.: PCT/JP2004/016767
§ 371 (c)(1),
(2), (4) Date: May 10, 2007

(87) PCT Pub. No.: WO2006/051595
PCT Pub. Date: May 18, 2006

(65) Prior Publication Data
US 2007/0287870 A1 Dec. 13, 2007

(51) Int. Cl.
C07C 45/00 (2006.01)
(52) U.S. Cl. .................................................. 568/347
(58) Field of Classification Search .................. 568/347
See application file for complete search history.

(56) References Cited

FOREIGN PATENT DOCUMENTS

| JP | 3-184935 | 8/1991 |
| JP | 7-267968 A | 10/1995 |
| JP | 2003-171335 A | 6/2003 |
| KR | 10-2000-0049811 | 8/2000 |

OTHER PUBLICATIONS

Indo Motoichi, "Synthetic Aromachemical-Chemistry and Commodity knowledge," The Chemical Daily Co., Ltd., Mar. 6, 1996, pp. 492-497.
"The Recently Technology on Synthetic Aromachemical," CMC Publishing, 1982, pp. 72-90.
K. Tanaka et al., "Catalytic Enantioselective Conjugate Addition of Chiral Alkoxydimethylcuprate to (E)-Cyclopentadec-2-enone," J. Chem. Soc. Perkin Trans. I, 1193 (1992).
A. Alexakis et al., "Catalytic Asymmetric Conjugate Addition on Macrocyclic and Acyclic Enones. Synthesis of R-(-)-Muscone," Letter, Synlett 1999, No. 11, pp. 1811-1813, ISSN 0936-5214, Thieme Stuttgart—New York.
D.S. Im et al., "A Newer Short Synthesis of dl-Muscone (I)," Journal of the Korean Chemical Society, 1996, vol. 40, No. 4, Printed in the Republic of Korea, pp. 243-248.
"Methoden Der Organischen Chemie (Houben-Weyl)," Band XII/2, Organische Phosphorverbindungen, G. Thieme Verlag Stuttgart, 1964, Part 2 (4th Ed.), pp. 99-105.
Leggy A. Arnold et al., "Enantioselective Catalytic Conjugate Addition of Dialkylzinc Reagents using Copper-Phosphoramidite Complexes; Ligand Variation and Non-linear Effects," Tetrahedron 56 (2000) 2865-2878, 2000 Elsevier Science Ltd.
Fu-Yao Zhang et al., "Enantioselective conjugate addition of diethylzinc to cyclic enones catalyzed by chiral copper complexes containing a new phosphours ligand with an $H_8$-binaphthoxy moiety," Tetrahedron: *Assymetry* 9 (1998) pp. 1179-1182.
Jean-Michel Brunel et al., "A New and Efficient Method for the Resolution of 1,1'-Binaphthalene-2,'-diol," J. Org. Chem. 1993, 58, pp. 7313-7314, 1993 American Chemical Society.
Yong Hyun Choi et al., "Copper-catalyzed conjugate addition on macrocyclic, cyclic, and acyclic enones with a chiral phosphoramidite ligand having a $C_2$-symmetric amine moiety," Tetrahedron: *Assymetry* 13 (2002) pp. 801-804.
Supplementary European Search Report issued in European Patent Application No. 04799627.7-1211 dated on May 23, 2008.
Frantz et al "Isotope Effects and the Mechanisms of Chlorotrimethylsilane-Mediated Addition of Cuprates to Enones" pp. 3288-3295 Journal of American Chemical Society vol. 122 No. 14, 2000.
Knopff et al "Tandem Asymmetric Conjugate Addition-Silylation of Enatiomericlally Enriched zinc Enolates. Synthetic Importance and Mechanistic Implications" pp. 3835-3837 Organic Letters vol. 4, No. 22 Oct. 4, 2002.
Iuliano et al "Deoxycholic Acid-based Phospites as Chiral Ligands in the Enantioselective Conjugate Addition of Dialkylzincs to Cyclic Enones: Preparation of (-)-(R)-muscone" pp. 2533-2538 Tetrahedron: Asymmetry 15 (2004).
Alexakis et al "Novel Biphenol Phosphoramidite Ligans for the Enantioselective Copper-Catalyzed Conjugate Addtiion of Dialkly Zincs" Synlett No. 9 pp. 1375-1378 (2001).

*Primary Examiner*—Sikarl A Witherspoon
(74) *Attorney, Agent, or Firm*—McDermott Will & Emery LLP

(57) ABSTRACT

A process for producing muscone by methyl addition to the 1,4-conjugation of 2-cyclopentadecenone. By the process, muscone is produced in high yield not under reaction condition including an extremely low temperature and a low concentration but under practical condition. The process comprises subjecting 2-cyclopentadecenone to a 1,4-conjugation addition reaction with an organometallic methylation reagent in the presence of a copper or nickel catalyst and an enol anion scavenger to obtain a 3-methyl-1-cyclopentadecene derivative represented by General Formula (II) and then solvolyzing the enol moiety of the 3-methyl-1-cyclopentadecene derivative to obtain muscone.

11 Claims, No Drawings

METHOD OF PRODUCING MACROCYCLIC KETONE, AND INTERMEDIATE THEREOF

RELATED APPLICATIONS

This application is the U.S. National Phase under 35 U.S.C. § 371 of International Application No. PCT/JP2004/016767, filed on Nov. 11, 2004, the disclosure of which Application is incorporated by reference herein.

TECHNICAL FIELD

The present invention relates to a method of producing a macrocyclic ketone muscone, in particular a method of producing muscone by 1,4-conjugation methyl-addition reaction of 2-cyclopentadecenone, and a new intermediate compound used in production thereof.

BACKGROUND ART

Recently the trend toward natural products of people has been rising, and in the field of the fragrance, there also arouses an interest for a musk-feeling fragrance having a higher aroma property and characteristically reminding of natural environment. Further, there is also a need for development of a new fragrance material derived from a natural compound or the same as or similar to a natural compound, from the point of safety for human beings and the environment.

Muscone is the principal fragrance component in natural musk and contained in the amount of 0.5 to 2.0% therein. Muscone was found out by Walbaum in 1906, and its chemical structure was determined by Ruzicka in 1926. Natural muscone is (−)-(R)-3-methylcyclopentadecanone, but its commercial product is a synthetic dl-isomer. When the fragrance of (−)-(R)-isomer and (+)-(S)-isomer is compared, the (R)-isomer has a diffusive stronger musk-feeling fragrance (threshold value: 3 ppm), while the (S)-isomer has a chemical, less-diffusive, poor and weak musk-feeling fragrance (threshold value: 10 ppm), and thus, the intensity of the fragrance of the (R)-isomer is known to be thrice greater than that of the (S)-isomer (see, for example, Non-patent Document 1 and Non-patent Document 2 below).

Non-patent Document 1: Indo Motoichi, "Synthetic Aromachemical—Chemistry and Commodity knowledge", The Chemical Daily, Mar. 6, 1996, pp. 492 to 497.

Non-patent Document 2: "Recently technology on Synthetic Aromachemical", CMC Publishing, 1982, pp. 72 to 90.

For the reasons above, there have been many reports of the studies on the method of preparing muscone, in particular, (−)-(R)-muscone. Among them, a method of producing an optically active muscone by 1,4-conjugation methyl-addition reaction of 2-cyclopentadecenone is considered to be promising, and there are recently some reports on the methods of preparing (−)-(R)-muscone in asymmetric methylation reaction using an optically active ligand. For example, it has been reported that it is possible to obtain favorable results by using a compound having an amino alcohol chiral auxiliary group containing a bornane skeleton in preparation (see Non-patent Document 3 below). However, the reported method of producing the (−)-(R)-muscone by using a chiral auxiliary group is yet to be commercialized, because it has disadvantages of demanding an extremely low reaction temperature of −78° C., an extended reaction time, and use of a chiral auxiliary group in an excessive amount of one equivalence or more. In another example, there is a report that a particular chiral phosphite compound gave a favorable result when various chiral phosphite ligands were examined in a catalytic amount (see Non-patent Document 4 below). However, the reported method shows a yield of 53% even at an inefficiently low concentration at a solvent/substrate rate of approximately 50 and thus, is not desirable. In yet another example, described is high-yield production of muscone by using a copper complex of 4-(cis-2,6-dimethylpiperidine) -(R)-dinaphthodioxaphosphepin or 4-(R,R-2,5-diphenyl-pyrrolidine) -(R)-dinaphthodioxaphosphepin as a chiral ligand (see Patent Document 1 below), but the literature does not disclose the reaction at higher concentration. When the reaction is carried out at higher concentration, conventional methods cause a problem of poor yield of the objective product by generation of high-molecular weight by-products. Further, the employment of an extreme reaction condition such as an extremely low temperature, a low concentration or an extended reaction period results in increase of a production cost. Low reaction yield also leads to increase of a production cost. Therefore, there exists an urgent need for a method of producing muscone economically at high yield without employing a reaction condition such as an extremely low temperature, a low concentration, or an extended reaction period.

Non-patent Document 3: J. Chem. Soc. Perkin Trans. I, 1193 (1992)

Non-patent Document 4: Synlett 1999, No. 11, pp. 1181-1183

Patent Document 1: Korean Patent Application Laid-Open No. 2001-49811

SUMMARY OF THE INVENTION

Problems to be Solved by the Invention

An object of the present invention, which has been made under the circumstances above, is to provide a method of producing muscone at high yield by 1,4-conjugation methyl-addition reaction of 2-cyclopentadecenone under a practical condition without employing an reaction condition such as extremely low temperature or low concentration.

Means for Solving the Problems

After intensive studies to solve the problems above, the inventors have found that it is possible to obtain the objective muscone in high yield under higher concentration by steps of forming a new enol derivative by trapping an enol anion generated by 1,4-conjugation methyl-addition reaction of 2-cyclopenta-decenone with a suitable scavenger while restraining the generation of by-products and then decomposing the enol derivative by a common method and after further studies, completed the present invention.

The present invention has the following aspects 1 to 13.

1. A method of producing muscone represented by the following Formula (I):

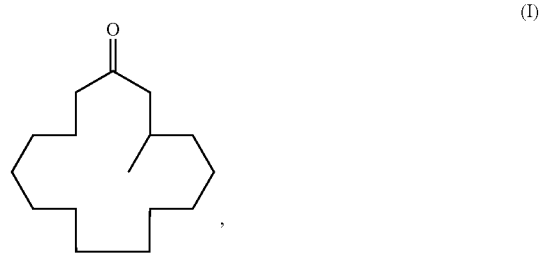

which comprises:

reacting 2-cyclopentadecenone represented by General Formula (III):

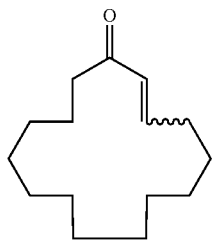

(III)

(wherein the wavy line represents a cis isomer and/or a trans isomer of double bond) with an organic metal methylation reagent via 1,4-conjugation addition reaction in the presence of a copper or nickel catalyst and an enol anion scavenger to give a 3-methyl-1-cyclopentadecene derivative represented by General Formula (II):

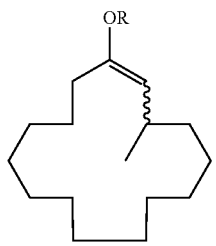

(II)

(wherein R represents a straight- or branched-chain acyl group which may have a substituent containing a heteroatom or an aromatic ring, an alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and the wavy line is the same as that above); and solvolyzing the enol moiety of the 3-methyl-1-cyclopentadecene derivative.

2. A method of producing an optically active muscone represented by Formula (I-a):

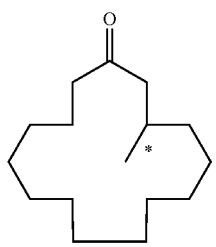

(I-a)

which comprises:

reacting 2-cyclopentadecenone represented by General Formula (III):

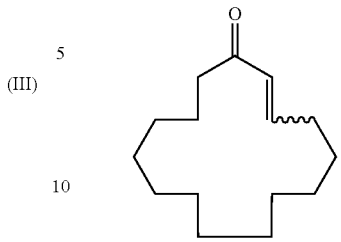

(III)

(wherein the wavy line represents a cis isomer and/or a trans isomer of double bond) with an organic metal methylation reagent via 1,4-conjugation addition reaction in the presence of a copper or nickel catalyst, an enol anion scavenger, and an optically active ligand to give an optically active 3-methyl-1-cyclopentadecene derivative represented by General Formula (II-a):

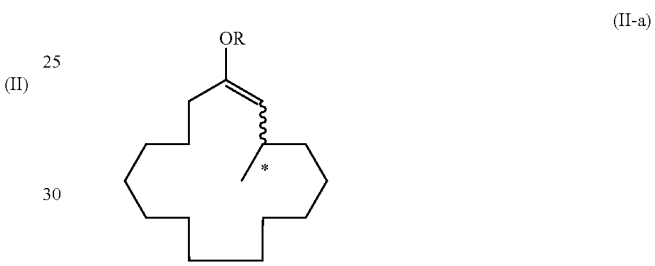

(II-a)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line is the same as that above); and solvolyzing the enol moiety of the optically active 3-methyl-1-cyclopentadecene derivative.

3. A method of producing a 3-methyl-1-cyclopentadecene derivative represented by General Formula (II):

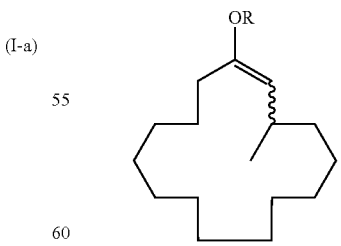

(II)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and the wavy line is the same as that above), which comprises reacting 2-cyclopentadecenone represented by General Formula (III):

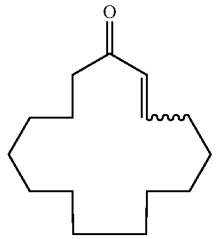

(III)

(wherein the wavy line represents a cis isomer and/or a trans isomer of double bond) with an organic metal methylation reagent via 1,4-conjugation addition reaction in the presence of a copper or nickel catalyst and an enol anion scavenger.

4. A method of producing an optically active 3-methyl-1-cyclopentadecene derivative represented by General Formula (II-a):

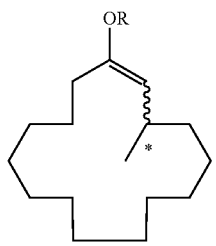

(II-a)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line is the same as that above), which comprises reacting 2-cyclopentadecenone represented by General Formula (III):

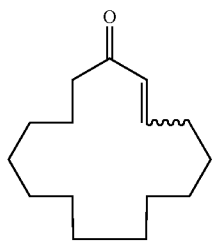

(III)

(wherein the wavy line represents a cis isomer and/or a trans isomer of double bond) with an organic metal methylation reagent via 1,4-conjugation addition reaction in the presence of a copper or nickel catalyst, an enol anion scavenger and an optically active ligand.

5. A method of producing muscone represented by Formula (I):

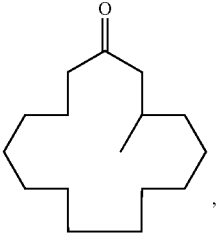

(I)

which comprises solvolyzing an enol moiety of a 3-methyl-1-cyclopentadecene derivative represented by General Formula (II):

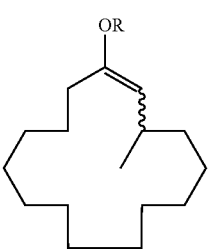

(II)

(wherein R represents a straight- or branched-chain acyl group which may have a substituent containing a heteroatom or an aromatic ring, a straight- or branched-chain alkyloxycarbonyl which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and the wavy line represents a cis isomer and/or a trans isomer of double bond).

6. A method of producing an optically active muscone represented by Formula (I-a):

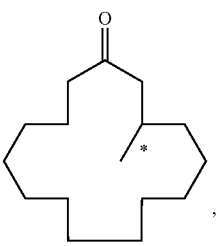

(I-a)

which comprises solvolyzing an enol moiety of an optically active 3-methyl-1-cyclopentadecene derivatives represented by General Formula (II-a):

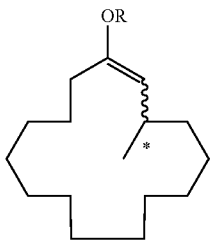

(II-a)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line represents a cis isomer and/or a trans isomer of double bond).

7. The production method according to the item 2 or 4 above, wherein the optically active ligand is an optically active ligand represented by General Formula (IV):

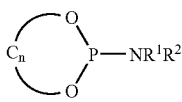

(IV)

(wherein $C_n$ represents a substituted or unsubstituted group having 2 to 4 carbon atoms, which forms a ring together with two oxygen atoms and a phosphorus atom; and $R^1$ and $R^2$ each independently represents a hydrogen atom or a chain or cyclic alkyl, aryl, alkanoyl or aralkyl group that may be substituted with a substituent or $R^1$ and $R^2$ represent groups that can form a heterocyclic ring together with an nitrogen atom connected thereto).

8. The production method according to the item 2 or 4 above, wherein the optically active ligand is an optically active ligand represented by General Formula (V):

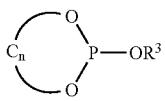

(V)

(wherein $C_n$ represents a substituted or unsubstituted group having 2 to 4 carbon atoms, which forms a ring together with two oxygen atoms and a phosphorus atom; and $R^3$ represents a hydrogen atom or a chain or cyclic alkyl, aryl, alkanoyl or aralkyl group that may be substituted with a substituent).

9. The production method according to the item 2 or 4 above, wherein the optically active ligand is 4-(cis-2,6-dimethyl-piperidine) -(R)-ditetrahydronaphthodioxaphosphepin, 4-(cis-2,6-dimethylpiperidine)-(R)-dinaphthodioxaphosphepin, 4-((R,R)-2,5-diphenylpyrrolidine)-(R)-dinaphthodioxa-phosphepin, or 4-((R,R)-2,5-diphenylpyrrolidine)-
(R)-ditetrahydronaphthodioxaphosphepin.

10. The production method according to the item 1, 2, 3, 4, 7 or 8 above, wherein the enol anion scavenger is an enol anion scavenger represented by the following General Formula (VI):

$$R^4-X \qquad (VI)$$

(wherein $R^4$ represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and X represents a halogen atom, an alkylsulfonyloxy group, an arylsulfonyloxy group, or OR' (wherein R' represents a straight- or branched-chain acyl group which may have a substituent containing a heteroatom or an aromatic ring, or a straight- or branched-chain alkyloxycarbonyl group which may have a substituent containing a heteroatom or an aromatic ring).

11. The production method according to the item 1, 2, 3, 4, 7 or 8 above, wherein the enol anion scavenger is an enol anion scavenger represented by the following General Formula (VII):

$$R^5-X \qquad (VII)$$

(wherein $R^5$ represents a straight- or branched-chain acyl group which may have a substituent containing a heteroatom or an aromatic ring, or a straight- or branched-chain alkyloxycarbonyl group which may have a substituent containing a heteroatom or an aromatic ring; and X represents a halogen atom, an alkylsulfonyloxy group, an arylsulfonyloxy group, or OR' (wherein R' represents a straight- or branched-chain acyl group which may have a substituent containing a heteroatom or an aromatic ring, or a straight- or branched-chain alkyloxycarbonyl group which may have a substituent containing a heteroatom or an aromatic ring).

12. A 3-methyl-1-cyclopentadecene derivative, represented by General Formula (II):

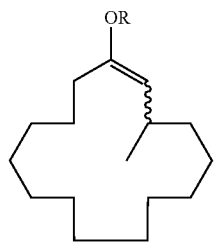

(II)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and the wavy line represents a cis isomer and/or a trans isomer of double bond).

13. An optically active 3-methyl-1-cyclopentadecene derivative, represented by General Formula (II-a):

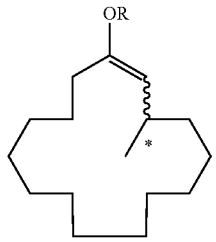

(II-a)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line represents a cis isomer and/or a trans isomer of double bond.

Advantageous Effects of the Invention

According to the present invention, it is possible to produce an objective muscone at high concentration and in high yield by trapping the enol anion generated by 1,4-conjugation methyl-addition reaction of 2-cyclopentadecenone to prepare a new enol derivative and then solvolyzing the enol moiety.

BEST MODE FOR CARRYING OUT THE INVENTION

Hereinafter the present invention will be described in detail.

In the present invention, as described above, 2-cyclopentadecenone represented by General Formula (III):

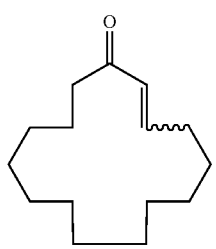

(III)

(wherein the wavy line represents a cis isomer and/or a trans isomer of double bond) is subjected to 1,4-conjugation addition reaction with an organic metal methylation reagent in the presence of a copper or nickel catalyst and an enol anion scavenger to give a 3-methyl-1-cyclopentadecene derivative represented by General Formula (II):

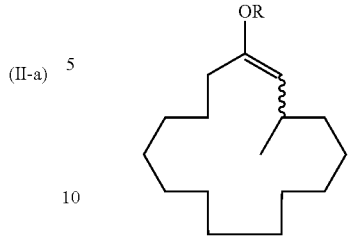

(II)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and the wavy line is the same as that above).

As an example of the 2-cyclopentadecenone represented by General Formula (III), which is used in this reaction, there is illustrated (E)-2-cyclopentadecenone, but the 2-cyclopentadecenone used in this reaction is not limited thereto. For example, (Z)-2-cyclopentadecenone or a mixture of its geometrical isomers may be also used. (E)-2-cyclopentadecenone can be prepared by a known method (see, for example, the following Patent Documents 2 and 3 and Non-patent Document 5) and a method similar to that. In the invention, any one of the compounds prepared by a known method or a method similar to that or commercially available may be used as the 2-cyclopentadecenone.

Patent Document 2: Japanese Patent Application Laid-Open (JP-A) No. 1-321556

Patent Document 3: JP-A No. 2001-369422

Non-patent Document 5: J. Korean Chem. Soc., 40, 243 (1996)

As the copper catalyst for use in the reaction, there can be used any one of copper catalysts traditionally used in the 1,4-conjugation methyl-addition reaction. Examples of the copper catalysts include copper (II) triflate (Cu (OTf)$_2$), copper (I) triflate (CuOTf), copper (II) acetylacetonate (Cu(acac)$_2$), copper (II) trifluoroacetate (Cu(OCOCF$_3$)$_2$), copper acetate (II) (Cu (OAc)$_2$), copper sulfate (II) (CuSO$_4$), cuprous chloride (CuCl), cupric chloride (CuCl$_2$), cuprous bromide (CuBr), cupric bromide (CuBr$_2$), cuprous iodide (CuI), cupric chloride (CuI$_2$), cuprous cyamide (CuCN), cuprous perchlorate (CuClO$_4$), cupric naphthenate (Cu(OCOC$_{10}$H$_9$)$_2$), copper (II) tetrafluoroborate (Cu (BF$_4$)$_2$), and tetrachlorocopper (II) dilithium (Li$_2$CuCl$_4$); and preferable are copper (II) triflate (Cu(OTf)$_2$), copper (I) triflate (CuOTf), and the like.

As the nickel catalyst for use in the reaction, there can be used any one of nickel catalysts traditionally used in the 1,4-conjugation methyl-addition reaction. Examples of the nickel catalysts include nickel acetylacetonate (Ni(acac)$_2$), nickel chloride (NiCl$_2$), nickel bromide (NiBr$_2$), nickel iodide (NiI$_2$), and nickel acetate Ni (OCOCH$_3$)$_2$; and preferable are nickel acetylacetonate (Ni(acac)$_2$), nickel chloride (NiCl$_2$), and the like.

Examples of the enol anion scavenger for use in the reaction include an enol anion scavenger represented by the following General Formula (VI):

$$R^4-X \qquad (VI)$$

(wherein R[4] represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and X represents a halogen atom, an alkylsulfonyloxy group, an arylsulfonyloxy group, or OR' (wherein R' represents a straight- or branched-chain acyl group which may have a substituent containing a heteroatom or an aromatic ring, or a straight- or branched-chain alkyloxycarbonyl group which may have a substituent containing a heteroatom or an aromatic ring)).

In General Formula (VI), examples of a straight- or branched-chain acyl group in the R[4], which may have a substituent containing a heteroatom or an aromatic ring, include acyl groups having one to three hydrogen atoms thereof that may be substituted with a lower alkyl group having 1 to 4 carbon atoms (such as a methyl group, an ethyl group, a propyl group, an isopropyl group, a n-butyl group, an isobutyl group, a sec-butyl group, and a tert-butyl group), a lower alkoxy group having 1 to 4 carbon atoms (such as a methoxy group, an ethoxy group, a propoxy group, an isopropoxy group, a n-butoxy group, an isobutoxy group, a sec-butoxy group, and a tert-butoxy group), a halogen atom (such as a fluorine atom, a chlorine atom, a bromine atom, or an iodine atom), a nitro group, and the like, such as a formyl group, an acetyl group, a chloroacetyl group, a dichloroacetyl group, a trichloroacetyl group, a trifluoroacetyl group, a propionyl group, a butyryl group, an isobutyryl group, a pivaloyl group, a valeryl group, an isovaleryl group, a hexanoyl group, an octanoyl group, a decanoyl group, a dodecanoyl group, a benzoyl group, a 4-trioil group, a 4-tert-butylbenzoyl group, a 4-anisoyl group, a 4-chlorobenzoyl group, and a 4-nitrobenzoyl group.

Examples of a straight- or branched-chain alkyloxycarbonyl group in the R[4], which may have a substituent containing a heteroatom or an aromatic ring, include alkyloxycarbonyl groups having one to three hydrogen atoms thereof that may be substituted with a lower alkyl group having 1 to 4 carbon atoms (such as a methyl group, an ethyl group, a propyl group, an isopropyl group, a n-butyl group, an isobutyl group, a sec-butyl group, and a tert-butyl group), a lower alkoxy group having 1 to 4 carbon atoms (such as a methoxy group, an ethoxy group, a propoxy group, an isopropoxy group, a n-butoxy group, an isobutoxy group, a sec-butoxy group, and a tert-butoxy group), a halogen atom (such as fluorine atom, chlorine atom, bromine atom, and iodine atom), a nitro group, and the like, such as a methoxycarbonyl group, an ethoxycarbonyl group, a propoxycarbonyl group, a butoxycarbonyl group, a tert-butoxycarbonyl group, an allyloxycarbonyl group, a benzyloxycarbonyl group, a p-chlorobenzyloxycarbonyl group, a p-bromobenzyloxycarbonyl group, a p-methoxybenzyloxycarbonyl group, and a p-nitro benzyloxycarbonyl group.

Examples of a straight- or branched-chain alkyl group in the R[4], which may have a substituent containing a heteroatom or an aromatic ring, include alkyl groups having 1 to 8 carbon atoms such as a methyl group, an ethyl group, a n-propyl group, an isopropyl group, a n-butyl group, an isobutyl group, a sec-butyl group, a tert-butyl group, a pentyl group, a hexyl group, a heptyl group, and an octyl group.

The alkyl group may have a substituent not participant in the reaction, and typical examples of the substituents include lower alkyl groups having 1 to 4 carbon atoms (such as a methyl group, an ethyl group, a n-propyl group, an isopropyl group, a n-butyl group, an isobutyl group, and a tert-butyl group), lower alkoxy groups having 1 to 4 carbon atoms (such as a methoxy group, an ethoxy group, a propoxy group, an isopropoxy group, a n-butoxy group, an isobutoxy group, a sec-butoxy group, and a tert-butoxy group), halogen atoms (such as a fluorine atom, a chlorine atom, a bromine atom, and an iodine atom), and a nitro group.

Examples of a straight- or branched-chain silyl group in the R[4], which may have a substituent containing a heteroatom or an aromatic ring, include tri-$C_{1-6}$ alkylsilyl groups such as a trimethylsilyl group, a triethylsilyl group, a triisopropylsilyl group, a dimethylisopropylsilyl group, a diethylisopropylsilyl group, a dimethyl(2,3-dimethyl-2-butyl)silyl group, a tert-butyldimethylsilyl group, and a dimethylhexylsilyl group), di-$C_{1-5}$ alkyl-$C_{6-18}$ arylsilyl groups (such as dimethylcumylsilyl group), di-$C_{6-18}$aryl-$C_{1-6}$alkylsilyl groups (such as tert-butyldiphenylsilyl group and diphenylmethylsilyl group), tri-$C_{6-18}$ arylsilyl groups (such as a triphenylsilyl group), and trisubstituted silyl groups including tri-$C_{7-19}$ aralkylsilyl groups (such as a tribenzylsilyl group and a tri-p-xylylsilyl group).

In the invention, among groups in the R[4]: a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, and a straight- or branched-chain silyl group which may have a substituent containing a heteroatom or an aromatic ring, the straight- or branched-chain acyl group which may have a substituent containing a heteroatom or an aromatic ring and the straight- or branched-chain alkyloxycarbonyl group which may have a substituent containing a heteroatom or an aromatic ring are preferable.

Preferable examples of the enol anion scavenger used in the present invention include acid anhydrides such as acetic anhydride, propionic anhydride, butanoic anhydride, pentanoic anhydride and benzoic anhydride; acid halides such as acetyl chloride, acetyl bromide, propionyl chloride, propionyl bromide, butyryl chloride, butyryl bromide, pentanoyl chloride, pentanoyl bromide, and benzoyl chloride; dicarbonates such as dimethyl dicarbonate, diethyl dicarbonate, dipropyl dicarbonate, and dibenzyl dicarbonate; trimethylsilyl chloride; and trimethylsilyl triflate. Particularly preferable among these are acid anhydrides such as acetic anhydride, propionic anhydride, butanoic anhydride, pentanoic anhydride, and benzoic anhydride; dicarbonates such as dimethyl dicarbonate, diethyl dicarbonate, dipropyl dicarbonate, and dibenzyl dicarbonate; and the like.

Examples of the organic metal methylation reagent used in the reaction include dimethylzinc ($ZnMe_2$), methylmagnesium chloride, methylmagnesium bromide, methylmagnesium iodide, methyllithium, and trimethylaluminum, and preferable are dimethylzinc ($ZnMe_2$) and the like.

As a solvent used in the reaction, any inert solvent being not participant in the reaction can be used. Preferable examples thereof are organic solvents including hydrocarbon solvents such as pentane, hexane, and heptane; aromatic solvents such as benzene, toluene, xylene, and mesitylene; ether solvents such as diethyl ether, diisopropyl ether, methyl-tert-butyl ether, dibutyl ether, cyclopentylmethyl ether, 1,2-dimethoxy-ethane, tetrahydrofuran, 1,4-dioxane, and 1,3-dioxolane; ester solvents such as methyl acetate, ethyl acetate, and butyl acetate; halogenated solvents such as methylene chloride, dichloroethane, and chlorobenzene: and mixed solvents comprising two or more thereof. Preferable among these are hydrocarbon solvents such as pentane, hexane, and heptane; aromatic solvents such as benzene, toluene, xylene, and mesitylene; and ether solvents such as diethyl ether, diisopropyl ether, methyl-tert-butyl ether, dibutyl ether, cyclopentylmethyl ether, 1,2-dimethoxyethane, tetrahydrofuran, 1,4-dioxane, and 1,3-dioxolane. The amount of the solvent used is normally one to 200-times by volume, preferably 5 to 100-times by volume, particularly preferably 10 to 50-times by volume, with respect to 1 part by weight of the 2-cyclopentadecenone represented by General Formula (III).

The copper catalyst and the nickel catalyst are used in the reaction in an amount of normally approximately 0.1 to 20 mol %, preferably approximately 1.0 to 10 mol %, with respect to 1 mole of the 2-cyclopentadecenone (III). The enol anion scavenger is used in an amount of normally approximately 1.0 to 5.0 moles, preferably approximately 1.2 to 3.0 moles, with respect to 1 mole of the 2-cyclopentadecenone (III). The organic metal methylation reagent is used in an amount of normally 1.0 to 5.0 moles, preferably 1.2 to 3.0 moles, with respect to 1 mole of the 2-cyclopentadecenone (III).

The reaction is carried out normally under an inert gas atmosphere such as nitrogen gas or argon gas. The reaction is carried out normally at a temperature of approximately −80° C. to 50° C., preferably at a temperature of approximately −30° C. to 30° C., normally approximately for 10 minutes to 20 hours, preferably approximately for 30 minutes to 10 hours. However these conditions may be altered as needed according to the reactive materials used and the amounts of the copper compound and others.

When racemic 3-methyl-cyclopentadecene derivatives are prepared in the reaction, a phosphorus-based ligand such as triphenylphosphine, tributylphosphine, tri-tert-butyl phosphine, triphenyl phosphite, or triethyl phosphite may be added as needed for smoother progress of the reaction. The ligand is used in an amount of normally approximately 1 to 10 mole equivalences, preferably approximately 1.5 to 5 mole equivalences, with respect to 1 mole of the copper or nickel catalyst.

An objective product can be isolated after the reaction by common post-treatment and as needed by a purification method such as distillation, recrystallization or column chromatography.

In the present invention, when a 3-methyl-1-cyclopentadecene derivative represented by General Formula (II) is produced from the 2-cyclopentadecenone represented by the above General Formula (III), by carrying out the reaction in the presence of an optically active ligand, it is possible to prepare an optically active 3-methyl-1-cyclopentadecene derivative represented by General Formula (II-a):

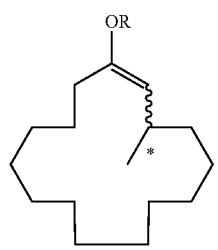

(II-a)

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line represents a cis isomer and/or a trans isomer of double bond).

The optically active ligand is not particularly limited, if it gives an optically active 3-methyl-1-cyclopentadecene (II) which is an objective compound. Examples of the optically active ligands used in the present invention include an optically active ligand represented by General Formula (IV):

(IV)

(wherein $C_n$ represents a substituted or unsubstituted group having 2 to 4 carbon atoms which can form a ring together with two oxygen atoms and one phosphorus atom; $R^1$ and $R^2$ each independently represent a hydrogen atom, a chain or cyclic alkyl, aryl, alkanoyl or aralkyl group that may be substituted with a substituent, or groups that can form a heterocyclic ring together with the nitrogen atom to which $R^1$ and $R^2$ are bound), and an optically active ligand represented by General Formula (V)

(V)

(wherein, $C_n$ is the same as that above; $R^3$ represents a hydrogen atom or a chain or cyclic alkyl, aryl, alkanoyl or aralkyl group that may be substituted with a substituent).

In the optically active ligands represented by General Formulae (IV) and (V), $C_n$ and/or $R^1$ and/or $R^2$ and/or $R^3$ are optically active groups or part of an optically active component. $C_n$ represents a $C_4$ chain (chain of four carbon atoms that may be substituted optionally) chirally substituted predominantly in a configuration, that has an enantiomer excess of preferably more than 95%, more preferably more than 99%, particularly preferably more than 99.5%. Preferably, $C_n$ forms a 7-membered ring having four carbon atoms together with two O atoms and one P atom, and the two pairs of carbons in the four carbon atoms form respectively part of an aryl group or a naphthyl group. Examples of the optically active ligand represented by General Formula (IV) favorably used in the present invention include the followings. However, the optically active ligand represented by General Formula (IV) is not limited to these typical examples. The optically active ligand represented by General Formula (IV) includes the constitutions of the enantiomers of the compounds represented as examples, and a desired constitution of the enantiomers is selected according to the optically activity of the objective product.

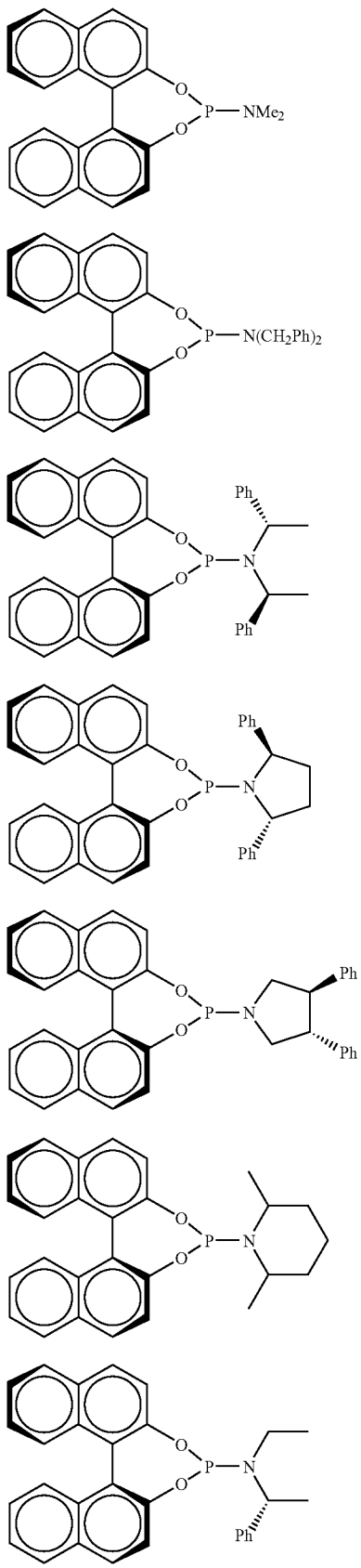
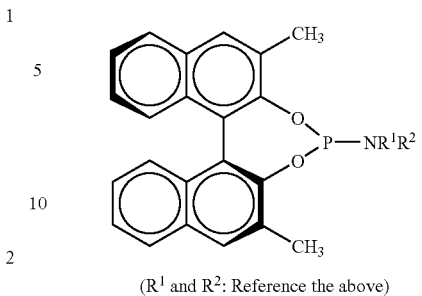
(R¹ and R²: Reference the above)
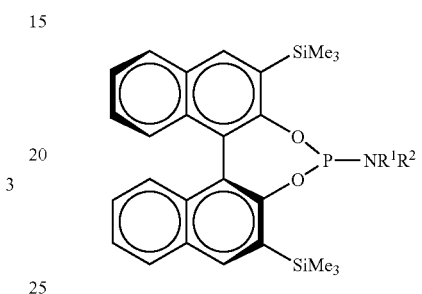
(R¹ and R²: Reference the above)
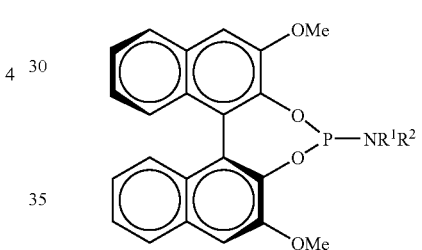
(R¹ and R²: Reference the above)
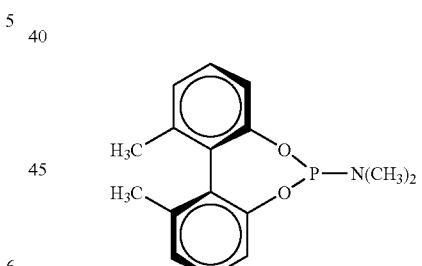
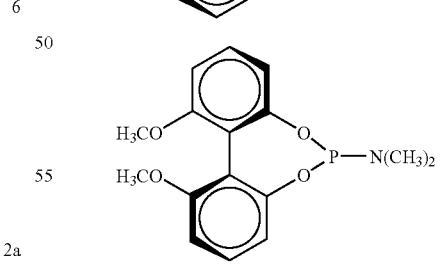
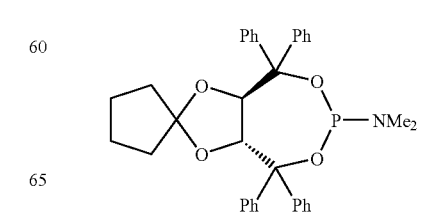

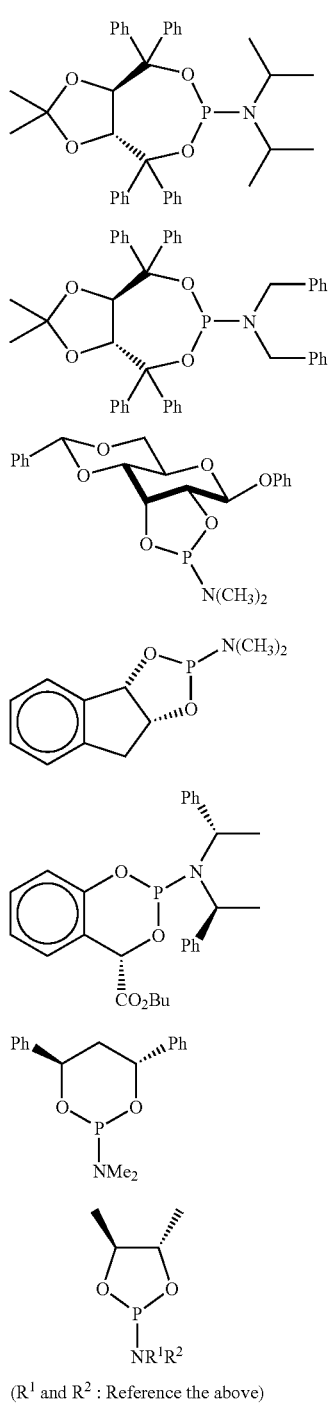
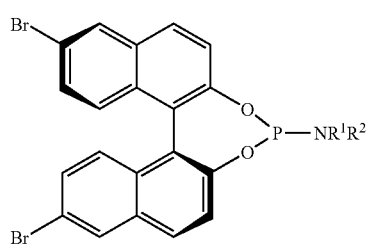
(R¹ and R² : Reference the above)
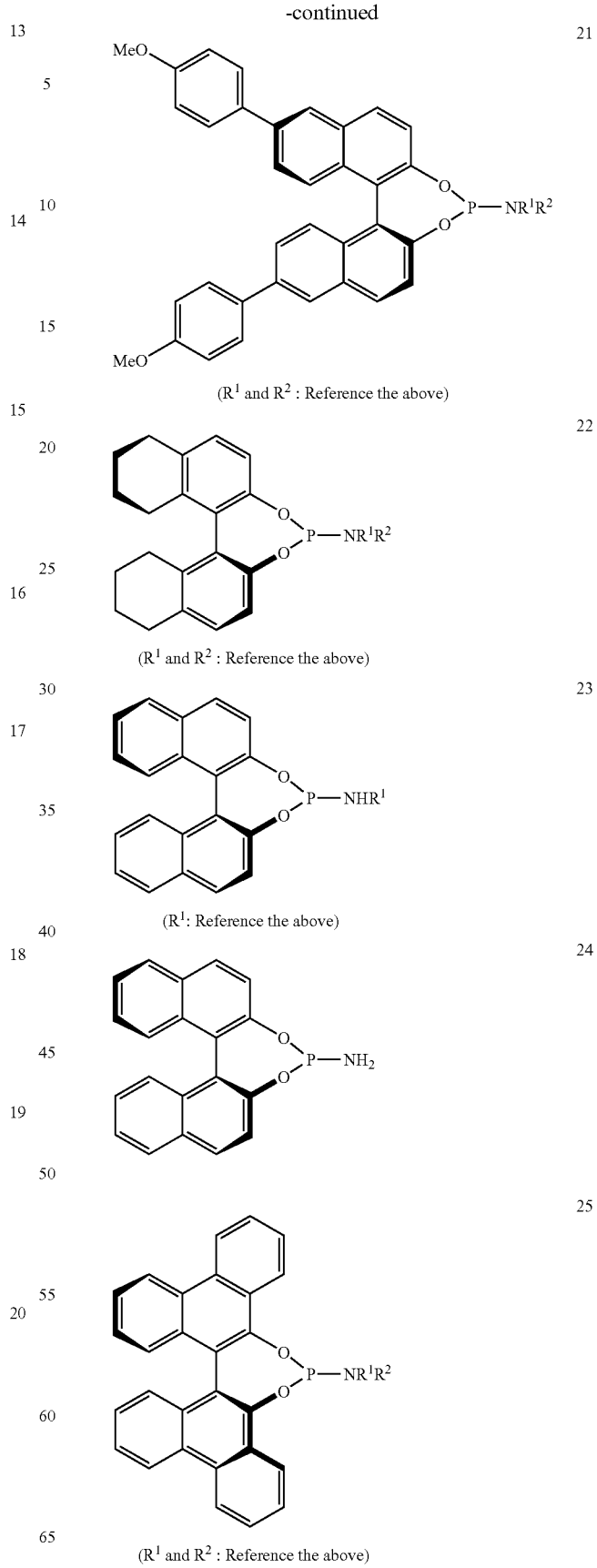

-continued

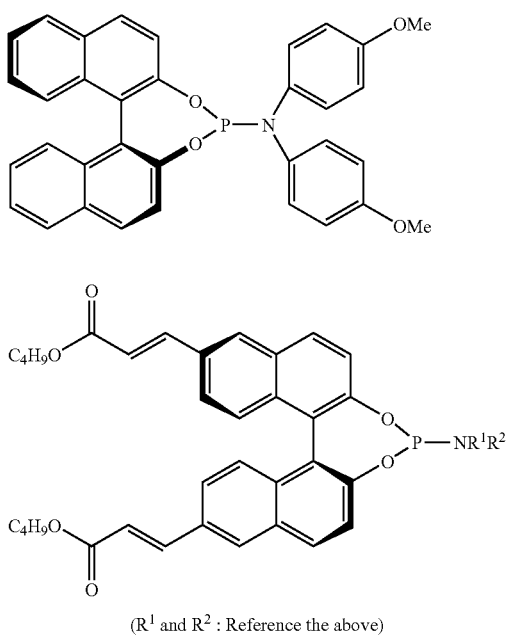

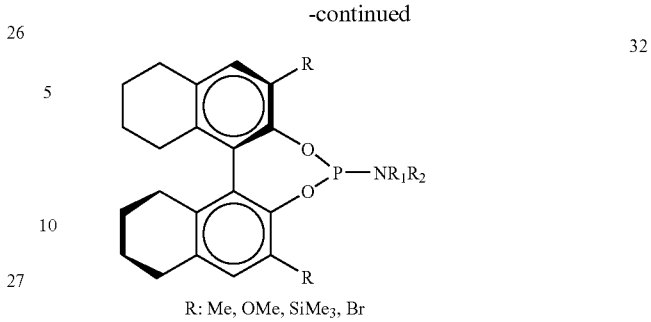

R: Me, OMe, SiMe₃, Br

As specific examples of compounds represented by General Formula (V), which is the optically active ligand favorably used in the present invention, there are illustrated above exemplified ligand compounds represented by General Formula (IV) wherein the NR¹R² moiety therein is substituted with an OR³ moiety. Examples of the optically active ligand represented by General Formula (V) include the followings. However, the optically active ligand represented by General Formula (V) is not particularly limited to these typical examples. The examples also include the constitutions of the enantiomers thereof and a desirable constitution of the enantiomers is selected according to the optically activity of the objective product.

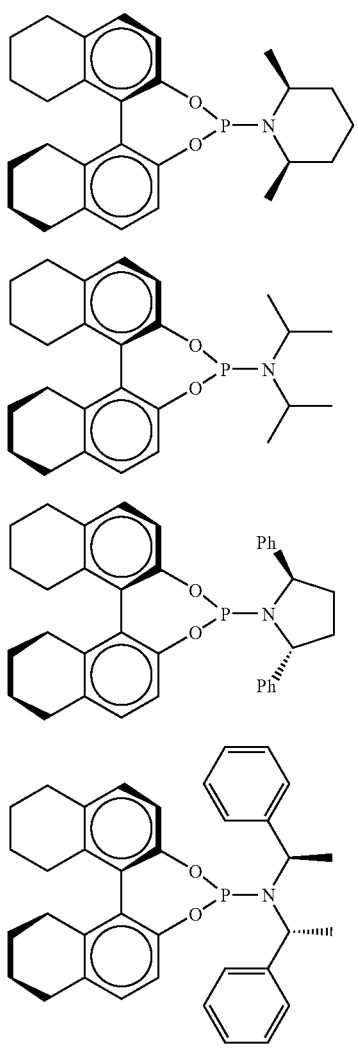

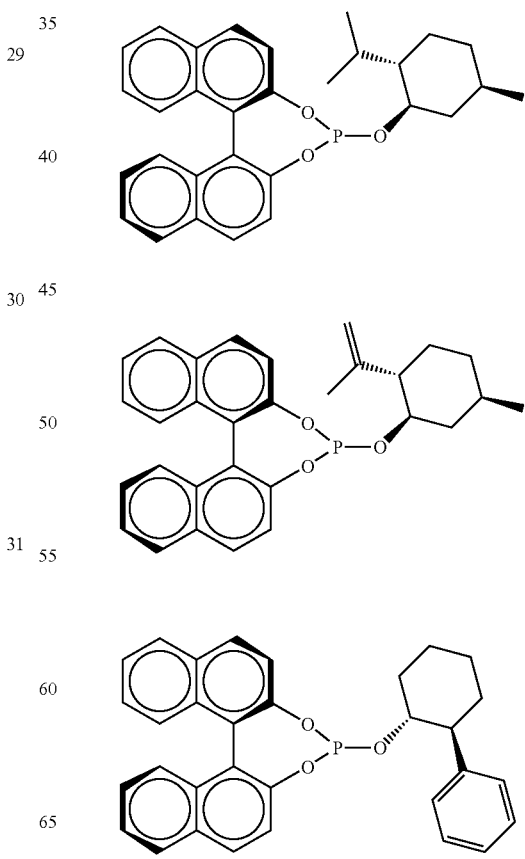

-continued

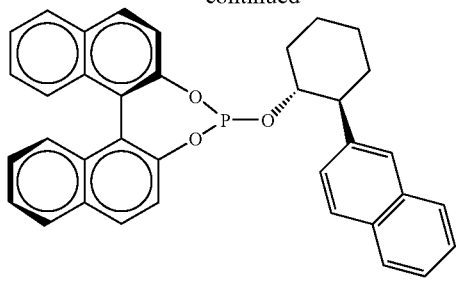

The optically active ligands represented by General Formulae (IV) and (V) are prepared easily by a known production method (see, for example, the following Non-patent Document 6).

Non-patent Document 6: Houben-Weyl Methoden der Organischen Chemie Band XII/2. Organische phosphor-verbindungen. G. Thieme Verlag, Stuttgart, 1964, Part 2 (4th Ed.), pp. 99-105.

In the first preferable production method described in Non-patent Document 6, a compound HO—$C_n$—OH is allowed to react with $P(NMe_2)_3$ or $P(NEt_2)_3$ (Me: methyl, and Et: ethyl), and then, with $R^1R^2NH$ or $R^3OH$ preferably in a solvent having a boiling point of 80° C. or higher, such as toluene. Examples of the catalyst favorable for the latter reaction include ammonium chloride, tetrazole, and benzimidazolium triflate. Examples of the compound HO—$C_n$—OH include chiral bisnaphthols such as (R)- or (S)-1,1'-bi(2-naphthol); chiral bisphenols such as (R)- or (S)-6,6'-dimethoxy-2,2'-bisphenol; diols such as (R,R)- or (S,S)-2,2'-dimethyl-1,3-dioxolane-4,5-bis-(1,1-diphenyl)-methanol (TADDOL) and (S,R)- or (R,S)-indane-1,2-diol; sugar-based 1,2- or 1,3-diols such as the compounds represented by the following Formula;

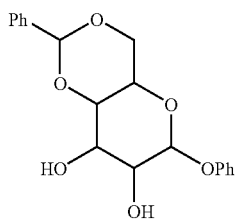

Examples of the $R^1R^2NH$ include benzylamine, dibenzylamine, diisopropylamine, dicyclohexylamine, 2,2,6,6-tetramethyl-piperidine, (R)- or (S)-1-methyl-benzylamine, piperidine, cis-2,6-dimethylpiperidine, (R,R)- or (S,S)-2,5-diphenyl-pyrrolidine, (R,R)- or (S,S)-3,4-diphenylpyrrolidine, morpholine, and (R,R)- or (S,S)-bis-(1-methylbenzyl)amine.

Examples of the $R^3OH$ include (1S,2R)- or (1S,2S)- or (1R,2R)- or (1R,2R)-2-phenylcyclohexanol, (1S,2R)- or (1S,2S)- or (1R,2R)- or (1R,2R)-2-(1-naphthyl)cyclohexanol, (1S,2R)- or (1S,2S)- or (1R,2R)- or (1R,2R)-2-(2-naphthyl)cyclohexanol, 1- or d-menthol, 1- or d-isopulegol, (R)- or (S)-1-phenylethanol, tert-butanol, fenchol, borneol, (S)- or (R)-2-hydroxydimethyl-4-tert-butyl-1,3-oxazoline, and (S)- or (R)-2-hydroxydimethyl-4-isopropyl-1,3-oxazoline.

The optically active ligand can also be prepared easily by another known production method (see, for example, Non-patent Documents 7 and 8 below) In this second favorable production method, a compound HO—$C_n$—OH is allowed to react with $PCl_3$ in the presence of a base such as $Et_3N$, and then, with $R^1R^2NLi$ in the presence of a solvent such as toluene or with $R^1R^2NH$ or $R^3OH$ in the presence of a base such as $Et_3N$. Examples of the HO—$C_n$—OH, $R^1R^2NH$ and $R^3OH$ are basically the same as those described in the first favorable production method.

Non-patent Document 7: Tetrahedron, 56, 2865 (2000)
Non-patent Document 8: Tetrahedron Asymmetry, 9, 1179 (1998)

The optically active ligand can be prepared easily by yet another known production method (see, for example, Non-patent Documents 9 and 10 below). In this third preferable production method, $R^1R^2NLi$, $R^1R^2NH$ or $R^3OH$ is allowed to react with $PCl_3$, and then, with a compound HO—$C_n$—OH preferably in the presence of a base such as $Et_3N$ and also in the presence of a solvent such as toluene. Examples of the HO—$C_n$—OH, $R^1R^2NH$ and $R^3OH$ are basically the same as those described above in the first preferable production method.

Non-patent Document 9: J. Org. Chem., 58, 7313 (1993)
Non-patent Document 10: Tetrahedron Asymmetry, 13, 801 (2002)

In the reactions described above, the optically active ligand represented by General Formula (IV) or (V) is used in an amount of normally approximately 0.1 to 20 mol %, preferably approximately 1.0 to 10 mol %, with respect to 1 mole of the 2-cyclopentadecenone (III).

The 3-methyl-1-cyclopentadecene derivative (II) obtained in the enol anion-trapping reaction described above is a new compound unknown in the art, and is a compound which is stable, normally oily or powdery, and storable. Thus, the 3-methyl-1-cyclopentadecene derivative (II) obtained in the enol anion-trapping reaction may be purified, for example, by distillation, recrystallization, or column chromatography, or may be stored without purification and used as it is withdrawn from the storage container when the following production process is conducted.

Specific examples of the compound represented by General Formula (II) include the following compounds. However, these compounds are illustrated only as examples, and the compounds represented by General Formula (II) are not limited to the following compounds.

(Enol Esters)

3-methyl-1-cyclopentadecenyl formate, 3-methyl-1-cyclopentadecenyl acetate, 3-methyl-1-cyclopentadecenyl propionate, 3-methyl-1-cyclopentadecenyl butyrate, 3-methyl-1-cyclopentadecenyl isobutyrate, 3-methyl-1-cyclopentadecenyl sec-butyrate, 3-methyl-1-cyclopentadecenyl tert-butyrate, 3-methyl-1-cyclopentadecenyl valerate, 3-methyl-1-cyclopentadecenyl isovalerate, 3-methyl-1-cyclopentadecenyl hexanoate, 3-methyl-1-cyclopentadecenyl heptanoate, 3-methyl-1-cyclopentadecenyl octanoate, 3-methyl-1-cyclopentadecenyl nonanate, 3-methyl-1-cyclopentadecenyl decanoate, 3-methyl-1-cyclopentadecenyl undecanoate, 3-methyl-1-cyclopentadecenyl dodecanoate, 3-methyl-1-cyclopentadecenyl benzoate, 3-methyl-1-cyclopentadecenyl chloroacetate, and 3-methyl-1-cyclopentadecenyl phenoxyacetate.

(Enol Carbonates)

3-methyl-1-cyclopentadecenyl methyl carbonate, 3-methyl-1-cyclopentadecenyl ethyl carbonate, 3-methyl-1-cyclopentadecenyl tert-butyl carbonate, and 3-methyl-1-cyclopentadecenyl benzyl carbonate.

(Enol Ethers) 3-methyl-1-cyclopentadecenyl methyl ether, 3-methyl-1-cyclopentadecenyl ethyl ether, 3-methyl-1-cyclopentadecenyl propyl ether, 3-methyl-1-cyclopentadecenyl isopropyl ether, 3-methyl-1-cyclopentadecenyl butyl ether, 3-methyl-1-cyclopentadecenyl isobutyl ether, and 3-methyl-1-cyclopentadecenyl benzyl ether.

(Silyl Enol Ethers) 3-methyl-1-cyclopentadecenyl trimethylsilyl ether, 3-methyl-1-cyclopentadecenyl triethylsilyl ether, and 3-methyl-1-cyclopentadecenyl tert-butyldiethylsilyl ether.

In the examples of the compounds, geometrical and optical isomers are not mentioned, but as the (E)-isomer, (Z)-isomer and a mixture of (E)- and (Z)-isomers thereof, as well as the (R)-isomer, (S)-isomer, and a mixture of (R)- and (S)-isomers thereof, there can be exemplified the above compounds similarly.

In the reaction, the configuration in geometrical isomerism of the 3-methyl-1-cyclopentadecene derivative represented by General Formula (II) is governed by that of the 2-cyclopentadecene represented by General Formula (III). For example, when the (E)-isomer of 2-cyclopentadecene represented by General Formula (III) is used, a (Z)-3-methyl-1-cyclopentadecene derivative is obtained mainly as the 3-methyl-1-cyclopentadecene derivative represented by General Formula (II).

In the reaction, the configuration on the 3-asymmetric carbon atom in the optically active 3-methyl-1-cyclopentadecene derivative represented by General Formula (II-a) obtained in the presence of an optically active ligand is controlled by that of the optically active ligand used in the reaction.

As a favorable example of the optically active ligand, there is illustrated 4-(cis-2,6-dimethylpiperidine)-(R)-ditetrahydronaphthodioxaphosphepin represented by the following Formula:

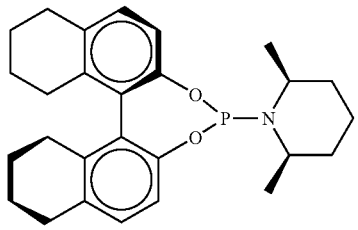

When it is used, a (R)-3-methyl-1-cyclopentadecene derivative is obtained as the optically active 3-methyl-1-cyclopentadecene derivative represented by General Formula (II-a). Other favorable examples of the optically active ligand include 4-(cis-2,6-dimethylpiperidine)-(R)-dinaphthodioxaphosphepin, 4-((R,R)-2,5-diphenylpyrrolidine)-(R)-dinaphthodioxa-phosphepin, and 4-((R,R)-2,5-diphenylpyrrolidine)-(R)-ditetrahydronaphthodioxaphosphepin, and similar results are obtained when these compounds are used.

In the present invention, subsequent solvolysis of the enol moiety of the 3-methyl-1-cyclopentadecene derivative represented by General Formula (II):

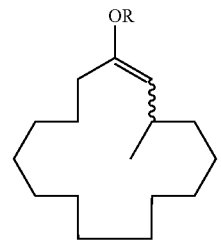

(wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; and the wavy line is the same as that above) gives muscone represented by Formula (I):

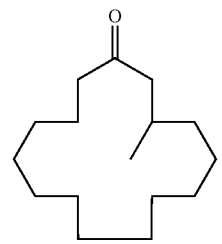

Any common known solvolytic method for enol compounds may be used as the solvolytic method of the invention. In the case of enol esters and enol carbonates, examples of the methods include a method of carrying out a reaction in a solvent in the presence of a basic catalyst. Examples of the basic catalyst used in this solvolysis include lithium hydroxide, sodium hydroxide, potassium hydroxide, magnesium hydroxide, calcium hydroxide, lithium carbonate, sodium carbonate, potassium carbonate, magnesium carbonate, calcium carbonate, lithium bicarbonate, sodium bicarbonate, potassium bicarbonate, lithium alkoxides (such as lithium methoxide, lithium ethoxide, and lithium tert-butoxide), sodium alkoxides (such as sodium methoxide, sodium ethoxide, and sodium tert-butoxide), and potassium alkoxides (such as potassium methoxide, potassium ethoxide, and potassium tert-butoxide). The basic catalysts are preferably sodium hydroxide, potassium hydroxide, sodium methoxide, sodium ethoxide and the like because they are cheaper and have favorable flexibility in use, higher selectivity in reaction, and high yield. These basic catalysts may be used alone or in combination of two or more thereof, but it is preferable to be used alone.

Alternatively in the case of enol ethers, the reaction may be carried out in a solvent in the presence of an acidic catalyst. Examples of the acidic catalyst used in the solvolysis include hydrofluoric acid, hydrochloric acid, hydrobromic acid, sulfuric acid, phosphoric acid, methanesulfonic acid, p-toluenesulfonic acid, acetic acid, chloroacetic acid, trifluoroacetic acid, and acidic ion-exchange resins. Favorable acidic catalysts include hydrochloric acid, sulfuric acid, and p-toluenesulfonic acid because they are cheaper, having favorable flexibility in use, and show higher reaction selectivity and high yield. These acidic catalysts may be used alone or in combination of two or more thereof, but it is preferable to be used alone.

For example in the case of silyl enol ethers, the reaction may be carried out in a solvent in the presence of the acidic catalyst above, and examples of the acidic catalysts further include fluorine compounds such as boron trifluoride and quaternary ammonium fluoride salts.

The solvent used in solvolysis is not particularly limited if it is a solvent allowing progress of solvolysis, and examples thereof include water, alcohols such as methanol, ethanol and isopropanol, and the mixed solvents thereof. Among the solvents above, methanol and ethanol are favorable because they are cheaper and have favorable flexibility in use, higher reaction selectivity and high yield.

Further, a cosolvent may be added as needed. The cosolvent is not particularly limited if it is inert to the reaction, and examples of such organic solvents include ether solvents such as diethyl ether, diisopropyl ether, tetrahydrofuran, dimethoxyethane, and dioxane; hydrocarbon solvents such as hexane, heptane and octane; and aromatic solvents such as benzene, toluene, and xylene.

The solvent is used in an amount of normally 0.5 to 100-times by volume, preferably 1 to 30-times by volume, with respect to 1 part by mass of the 3-methyl-1-cyclopentadecene derivative (II). The reaction is carried out at normally approximately 0 to 250° C., preferably approximately 20 to 100° C., normally approximately for 10 minutes to 20 hours, preferably approximately for 30 minutes to 10 hours, but these conditions may be altered properly according to the amount of the solvent and catalyst used.

The objective product may be isolated as needed after reaction by common post-treatment such as distillation or column chromatography. The reaction may be carried out either batchwise or continuously in the invention.

Solvolysis of the enol moiety in the 3-methyl-1-cyclopentadecene derivative represented by General Formula (II) has been described above in detail. And the catalyst, solvent, reaction condition and the like in solvolysis of the optically active 3-methyl-1-cyclopentadecene derivative represented by General Formula (II-a) are the same as those described above. Thus, it is possible to prepare optically active muscone represented by General Formula (I-a) by solvolysis of the optically active 3-methyl-1-cyclopentadecene derivative represented by General Formula (II-a) in a similar manner.

In the reaction, the configuration of the 3-asymmetric carbon atom on the optically active muscone represented by Formula (I-a) retains that of the optically active 3-methyl-1-cyclopentadecene derivative represented by General Formula (II-a). Thus, for example, when a (R)-3-methyl-1-cyclopentadecene derivative is used as the optically active 3-methyl-1-cyclopentadecene derivative represented by General Formula (II-a), (R)-muscone is obtained as muscone represented by Formula (I-a) in retaining an optical purity. The configuration of the optically active 3-methyl-1-cyclopentadecene derivative is controlled by that of the optically active ligand used in the reaction.

EXAMPLE

Hereinafter, the present invention will be described in detail with reference to Examples and Comparative Examples, but it should be understood that the present invention is not restricted thereby and various modifications are possible within the scope of the present invention.

In the following description, "%" means "% by mass" unless specified otherwise.

Analysis in the Examples and Comparative Examples below was conducted by using the following analytical instruments:

Optical Rotatory Power;
  Instrument: P-1020 (manufactured by JASCO Corp.)

Proton nuclear magnetic resonance spectrum ($^1$H-NMR);
  Instrument: DRX-500 (manufactured by Bruker Corp.)
  Internal standard substance: tetramethylsilane Infrared absorption spectrum (IR);
  Instrument: Nicolet AVATAR 360 FT-IR (manufactured by Nicolet Japan Corporation)

Mass spectrum (MS);
  Instrument: GCMS-QP2010 (manufactured by Shimadzu Corporation)

Gas Chromatography:
  Instrument: GC-14 A (manufactured by Shimadzu Corporation)
  Column: Rtx-1 (0.25 mm×60 m) (manufactured by RESTEK Corporation)

High-Performance Liquid Chromatography (HPLC):
  Instrument: Waters 2695 (manufactured by Japan Waters K.K.)
  Column: CHIRALPAK™ AS-H (0.25 cmϕ×25 cm) (Daicel Chemical Industries, Ltd.)

Example 1

Synthesis of (R)-3-methyl-1-cyclopentadecenyl propionate

To a 1,000 ml reaction flask 1.32 g (2.9 mmol) of an optically active ligand 4-(cis-2,6-dimethylpiperidine)-(R)-ditetra-hydronaphthodioxaphosphepin, 0.47 g (1.3 mmol) of Cu(OTf)$_2$, 115 ml (230 mmol) of a dimethylzinc toluene solution (2.0 mol/L), and 524 g of xylene were added and cooled to −20° C. under a nitrogen atmosphere. Then, 20.6 g (158 mmol) of propionic anhydride and 32 g (144 mmol) of (2E)-cyclopentadecenone were added thereto dropwise over 3 hours. After dropwise addition, the mixture was stirred for 4 hours until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 43.2 g of a crude product. The concentrated solution was distilled (boiling point: 112° C./39.9 Pa) to give 39.4 g (134 mmol) of the title compound (yield: 93%). Gas chromatographic analysis gave E/Z=1.0/99.0.

$^1$H-NMR (500 MHz, CDCl$_3$, δ): 0.90 (3H, d, J=12.5 Hz), 1.07 to 1.15 (2H, m), 1.20 (3H, t, J=7.6 Hz), 1.26 to 1.40 (15H, m), 2.14 to 2.16 (1H, m), 2.30 to 2.39 (2H, m), 2.40 (2H, q, J=7.6 Hz), 4.77 (1H, d, J=9.6 Hz)

MS m/z: 293 (M$^+$5), 265 (3), 238 (90), 220 (30), 209 (27), 195 (13), 180 (11), 158 (7), 142 (7), 125 (38), 117 (28), 97 (60), 84 (55), 69 (62), 57 (100), 41 (37)

IR ν$_{max}$ (cm$^{-1}$): 2926, 2856, 1152

[α]$_D$: −79.2° (c=1.0 (in CHCl$_3$))

Example 2

Synthesis of (R)-muscone

To a 200-ml round-bottomed flask 27.3 g (93 mmol) of (R)-3-methyl-1-cyclopentadecenylpropionate obtained in Example 1 and 54.6 g of toluene were added and stirred. 17.9 g (93 mmol) of a methanolic 28% sodium methoxide solution was added dropwise at 20° C., and the mixture was stirred additionally for 1 hour until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 29.4 g of crude (R)-muscone. The concentrated solution was distilled (boiling point: 110° C./50.5 Pa) to give 21.4 g (90 mmol) of the title compound (yield: 97%). The optical purity thereof as determined by high-performance liquid chromatography was 83% ee.

Example 3

Synthesis of (R)-3-methyl-1-cyclopentadecenyl acetate

Under a nitrogen atmosphere 3.30 g (7.25 mmol) of an optically active ligand 4-(cis-2,6-dimethylpiperidine)-(R)-ditetrahydronaphthodioxaphosphepin, 1.31 g (3.62 mmol) of Cu(OTf)$_2$, 217 ml (0.43 mol) of a dimethylzinc toluene solution (2.0 mol/l), and 1420 g of toluene were added to a 2,000-ml reaction flask and stirred. Then, 37.0 g (0.36 mol) of acetic anhydride was added thereto at −20° C., and then 79.8 g (0.36 mol) of (2E)-cyclopentadecenone was added thereto dropwise over 1 hour. After dropwise addition, the mixture was stirred for 6 hours until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 152 g of a crude product. The concentrated solution was distilled (boiling point: 103° C./0.3 mm Hg) to give 94.8 g (0.34 mol) of the title compound (yield: 94%). Gas chromatographic analysis there of gave E/Z=0.3/99.7.

$^1$H-NMR (500 MHz, CDCl$_3$, δ): 0.93 (3H, d, J=6.8 Hz), 1.07 to 1.15 (2H, m), 1.20 to 1.60 (20H, m), 2.15 to 2.18 (1H, m), 2.16 (3H, s), 2.28 to 2.40 (2H, m), 4.79 (1H, d, J=9.6 Hz)

MS m/z: 280 (M$^+$3), 265 (3), 238 (100), 220 (30), 209 (25), 195 (18), 180 (10), 156 (9), 142 (9), 125 (48), 112 (30), 97 (85), 84 (72), 69 (98), 55 (60), 43 (82)

IR $v_{max}$ (cm$^{-1}$): 2927, 2856, 1755, 1458, 1214

[α]$_D$: −82.2° (C=1.0 (in CHCl$_3$))

Example 4

Synthesis of (R)-muscone (R)-muscone was prepared under the same condition as that in Example 2 except that the (R)-3-methyl-1-cyclopentadecenyl acetate obtained in Example 3 was solvolyzed instead of the (R)-3-methyl-1-cyclopentadecenyl propionate in Example 2. The yield was 97%. The optical purity thereof as determined by high-performance liquid chromatography was 82% ee.

Example 5

Synthesis of (R)-3-methyl-1-cyclopentadecenyl acetate and (R)-muscone

Under a nitrogen atmosphere 55 mg (0.121 mmol) of an optically active ligand 4-(cis-2,6-dimethylpiperidine)-(R)-ditetrahydronaphthodioxaphosphepin, 14.5 mg (0.04 mmol) of Cu(OTf)$_2$, 2.55 ml (4.8 mmol) of a dimethylzinc toluene solution (1.88 mol/L), and 5 ml of toluene were added to a 30-ml reaction flask and cooled to −20° C. Then, a mixed solution containing 410 mg (4 mmol) of acetic anhydride, 889 mg (4 mmol) of (2E)-cyclopentadecenone and 5 ml of toluene was added thereto dropwise over 5 minutes, and the resultant mixture was stirred additionally for 4 hours until completion of the reaction was determined by gas chromatographic analysis. The reaction was terminated by addition of an aqueous 5% sulfuric acid solution after completion of the reaction to give 1.2 g of crude (R)-3-methyl-1-cyclopentadecenyl acetate.

The mixture obtained was solvolyzed in a methanolic 28% sodium methoxide solution to give 0.88 g (3.7 mmol) of (R)-muscone (yield: 92%).

Comparative Example 1

Synthesis of (R)-muscone (R)-muscone was prepared directly under the same reaction condition as that in Example 5 except that no acetic anhydride was used. The yield was 53%.

As apparent from the comparison between Example 5 and Comparative Example 1, the reaction yield was definitely increased when muscone was prepared via an enol isomer 3-methyl-1-cyclopentadecene derivative (II) obtained by the reaction caused by addition of an enol anion scavenger, acetic anhydride.

Example 6

Synthesis of (R)-3-methyl-1-cyclopentadecenyl butyrate and (R)-muscone

To a 100-ml reaction flask 45.8 mg (0.10 mmol) of an optically active ligand 4-(cis-2,6-dimethylpiperidine)-(R)-ditetrahydronaphthodioxaphosphepin, 16.4 mg (0.045 mmol) of Cu(OTf)$_2$, 8.0 ml (16 mmol) of a dimethylzinc toluene solution (2.0 mol/L), and 36 g of xylene were added and stirred. 1.7 g (11 mmol) of n-butanoic anhydride was added thereto at −20° C. and then, 2.2 g (10 mmol) of (2E)-cyclopentadecenone was added dropwise over 1 hour. After dropwise addition, the mixture was stirred additionally for 4 hours until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 3.0 g of a crude product. The concentrated solution was purified by silica gel column chromatography to give 2.8 g (9.1 mmol) of (R)-3-methyl-1-cyclopentadecenyl butyrate (yield: 91%). Gas chromatographic analysis thereof gave E/Z=3.8/96.2.

$^1$H-NMR (500 MHz, CDCl$_3$, δ): 0.92 (3H, d, J=6.8 Hz), 1.00 (3H, t, J=7.4 Hz), 1.09 to 1.43 (23H, m), 1.71 (2H, q, J=7.4 Hz), 2.13 to 2.17 (1H, m), 2.29 to 2.38 (2H, m), 2.40 (2H, t, J=7.4 Hz), 4.77 (1H, d, J=9.6 Hz)

MS m/z: 307 (M$^+$5), 265 (3), 238 (95), 220 (27), 209 (23), 195 (10), 180 (8), 156 (5), 142 (5), 125 (45), 117 (30), 97 (53), 84 (50), 71 (100), 55 (45), 43 (96)

IR $v_{max}$ (cm$^{-1}$): 2928, 2857, 1240, 1153, 1103

The (R)-3-methyl-1-cyclopentadecenyl butyrate obtained was then solvolyzed into (R)-muscone, and the optical purity thereof as determined by high-performance liquid chromatography was 85.5% ee.

Example 7

Synthesis of (R)-3-methyl-1-cyclopentadecenyl isobutyrate and (R)-muscone

A crude product was prepared under the same condition as that in Example 6 except that isobutanoic anhydride was used instead of n-butanoic anhydride and xylene was used in an amount of 14 g, and was purified and isolated by silica gel column chromatography to give 2.5 g (8.14 mmol) of the title compound (R)-3-methyl-1-cyclopentadecenyl isobutyrate (yield: 81%). Gas chromatographic analysis thereof gave E/Z=1.4/98.6.

$^1$NMR (500 MHz, CDCl$_3$, δ): 0.91 (3H, d, J=6.8 Hz), 1.06 to 1.40 (30H, m), 2.13 to 2.16 (1H, m), 2.30 to 2.40 (2H, m), 2.63 to 2.69 (2H, m), 4.77 (1H, d, J=9.6 Hz)

MS m/z: 307 (M$^+$5), 265 (5), 238 (35), 220 (22), 209 (12), 195 (12), 180 (3), 156 (5), 142 (5), 125 (15), 117 (8), 97 (20), 84 (20), 71 (95), 55 (23), 43 (100)

IR $v_{max}$ (cm$^{-1}$): 2927, 2857, 1236, 1181, 1139, 1058

The compound was then solvolyzed into (R)-muscone similarly as Example 6, and the optical purity thereof as determined by high-performance liquid chromatography was 85.7% ee.

Example 8

Synthesis of (R)-3-methyl-1-cyclopentadecenylmethyl carbonate and (R)-muscone 2.36 g (0.80 mmol) of a title compound (R)-3-methyl-1-cyclopentadecenylmethyl carbonate was obtained (yield: 80%) by preparing a crude product under the same condition as that in Example 7 except that dimethyl dicarbonate was used instead of isobutanoic anhydride and purifying it by silica gel column chromatography. Gas chromatographic analysis thereof gave E/Z =1.2/98.8.

$^1$H-NMR (500 MHz, CDCl$_3$, δ): 0.94 (3H, d, J=6.8 Hz), 1.05 to 1.53 (22H, m), 2.12 to 2.19 (1H, m), 2.38 to 2.39 (2H, m), 3.82 (3H, S), 4.78 (1H, d, J=9.7 Hz)

MS m/z: 296 (M+3), 281 (3), 264 (2), 237 (5), 220 (70), 205 (8), 191 (8), 178 (10), 163 (7), 149 (20), 135 (25), 121 (32), 111 (73), 94 (100), 80 (82), 69 (90), 55 (90), 41 (78)

IR $v_{max}$ (cm$^{-1}$): 2928, 2857, 1760, 1457, 1440, 1241

The compound was then solvolyzed into (R)-muscone similarly as Example 7, and the optical purity thereof as determined by high-performance liquid chromatography was 85.5% ee.

Example 9

Synthesis of 3-methyl-1-cyclopentadecenyltrimethylsilyl ether

Under a nitrogen atmosphere 47.8 mg (0.154 mmol) of triphenyl phosphite, 25.3 mg (0.07 mmol) of Cu(OTf)$_2$, 9.5 ml (19 mmol) of a dimethylzinc toluene solution (2.0 mol/L), and 20 g of xylene were added to a 100-ml reaction flask and stirred. 0.84 g (7.7 mmol) of trimethylsilane chloride was added thereto at −20° C. and 0.78 g (7.7 mmol) of triethylamine and 1.56 g (7.0 mmol) of (2E)-cyclopentadecenone were added dropwise over 1 hour. After dropwise addition, the mixture was stirred additionally for 4 hours until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 2.5 g of a crude product. The concentrated solution was purified by silica gel column chromatography to give 1.74 g (5.59 mmol) of the title compound (yield: 80%). Gas chromatographic analysis gave E/Z=25/75.

$^1$H-NMR (500 MHz, CDCl$_3$, δ): 0.18 (9H, s), 0.91 (3H, d, J=6.8 Hz), 1.03 to 1.09 (2H, m), 1.13 to 1.68 (20H, m), 1.98 to 2.06 (2H, m), 2.43 to 2.46 (1H, m), 4.20 (1H, d, J=9.3 Hz)

MS m/z: 310 (M$^+$28), 295 (40), 281 (5), 267 (13), 253 (5), 239 (3), 225 (5), 221 (10), 197 (20), 183 (5), 169 (68), 157 (38), 143 (25), 130 (57), 109 (2), 95 (5), 73 (100), 69 (10), 55 (13), 41 (12)

IR $v_{max}$ (cm$^{-1}$): 2926, 2857, 1670, 1457, 1251, 843

Example 10

Synthesis of 3-methyl-1-cyclopentadecenyl propionate

Under a nitrogen atmosphere 41.0 mg (0.13 mmol) of triphenyl phosphite, 21.7 mg (0.06 mmol) of Cu(OTf)$_2$, 4.84 ml (9.6 mmol) of a dimethylzinc toluene solution (2.0 mol/l), and 9 g of xylene were added to a 100-ml reaction flask and stirred. 0.86 g (6.6 mmol) of propionic anhydride and 1.33 g (6.0 mmol) of (2E)-cyclopentadecenone were added thereto dropwise over 3 hours at −20° C. After dropwise addition, the mixture was stirred additionally for 4 hours until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 63 g of a crude product. The concentrated solution was purified by silica gel column chromatography to give 1.59 g (5.4 mmol) of the title compound (yield: 90%). Gas chromatographic analysis gave E/Z =1.0/99.0.

Example 11

Synthesis of (R)-3-methyl-1-cyclopentadecenyl propionate and (R)-muscone

Under a nitrogen atmosphere 0.14 g (0.25 mmol) of an optically active ligand 4-((R,R)-2,5-diphenylpyrrolidine)-(R)-dinaphthodioxaphosphepin (see Non-patent Document 10), 43.2 mg (0.12 mmol) of (CuOTf)$_2$-toluene, 4.84 ml (9.6 mmol) of a dimethylzinc toluene solution (2.0 mol/L), and 15 g of toluene were added to a 100-ml reaction flask and stirred. 0.86 g (6.6 mmol) of propionic anhydride and 1.33 g (6.0 mmol) of (2E)-cyclopentadecenone were added thereto dropwise at −40° C. over 3 hours. After dropwise addition, the mixture was stirred additionally for 4 hours until completion of the reaction was determined by gas chromatographic analysis. The reaction was terminated by addition of an aqueous 5% sulfuric acid solution after completion of the reaction; the reaction solution was phase-separated and washed with water; and then, the solvent was evaporated under reduced pressure to give 63 g of a crude product. The concentrated solution was purified by silica gel column chromatography to give 1.63 g (5.5 mmol) of (R)-3-methyl-1-cyclopentadecenyl propionate (yield: 92%). Gas chromatographic analysis thereof gave E/Z=1.0/99.0.

The product was solvolyzed into (R)-muscone, and the optical purity determined was 95.0% ee.

Example 12

Synthesis of 3-methyl-1-cyclopentadecenyl acetate and (R)-muscone (R)-3-methyl-1-cyclopentadecenyl acetate was obtained at a yield of 91% by preparing a crude product in the same manner as in Example 11 except that an equimolar amount of 4-(cis-2,6-dimethylpiperidine)-(R)-dinaphthodioxaphosphepin (see Patent Document 1) was used instead of the optically active ligand used in Example 11, an equimolar amount of acetic anhydride was used instead of propionic anhydride, and reaction was conducted at −30° C. and isolating the product by silica gel column chromatography. Gas chromatographic analysis thereof gave E/Z =0.3/99.7.

The product was solvolyzed into (R)-muscone, and the optical purity thereof as determined by high speed liquid chromatography was 89.0% ee.

INDUSTRIAL APPLICABILITY

Muscone obtained by the production method according to the present invention is a compound useful as a fragrance, a raw material for medicine, or the like.

The invention claimed is:

1. A method of producing muscone represented by the following Formula (I):

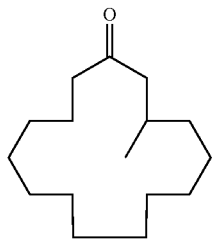

(I)

the method comprising:
reacting 2-cyclopentadecenone represented by General Formula (III):

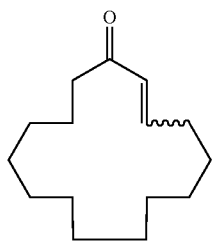

(III)

wherein the wavy line represents a cis isomer and/or a trans isomer of double bond, with an organic metal methylation reagent via 1,4-conjugation addition reaction in the presence of a copper or nickel catalyst and an enol anion scavenger to give a 3-methyl-1-cyclopentadecene derivative represented by General Formula (II):

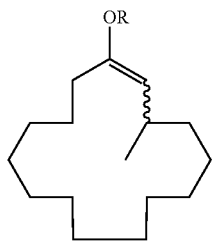

(II)

wherein R represents a straight- or branched-chain acyl group which may have a substituent containing a heteroatom or an aromatic ring, an alkyloxycarbonyl group which may have a substituent containing a heteroatom or an aromatic ring, or a straight- or branched-chain alkyl group which may have a substituent containing a heteroatom or an aromatic ring; and the wavy line is the same as that above; and solvolyzing the enol moiety of the 3-methyl-1-cyclopentadecene derivative.

2. A method of producing optically active muscone represented by Formula (I-a):

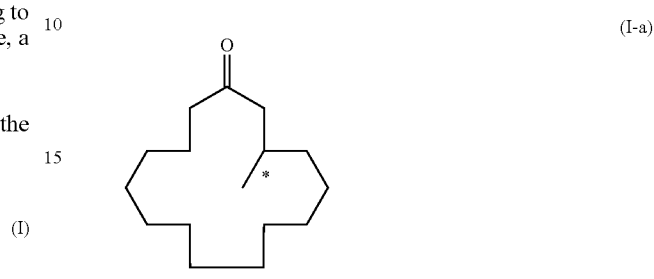

(I-a)

the method comprising:
reacting 2-cyclopentadecenones represented by General Formula (III):

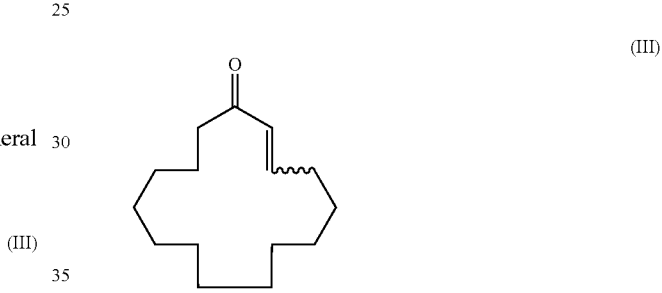

(III)

wherein the wavy line represents a cis isomer and/or a trans isomer of double bond, with an organic metal methylation reagent via 1,4-conjugation addition reaction in the presence of a copper or nickel catalyst, an enol anion scavenger, and an optically active ligand to give an optically active 3-methyl-1-cyclopentadecene derivative represented by General Formula (II-a):

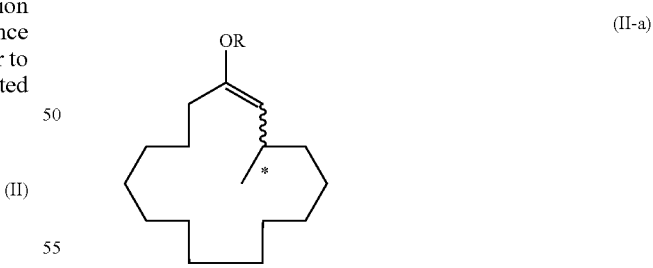

(II-a)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring;* represents an asymmetric carbon atom; and the wavy line is the same as that above; and solvolyzing the enol moiety of the optically active 3-methyl-1-cyclopentadecene derivative.

3. A method of producing muscone represented by Formula (I):

the method comprising solvolyzing an enol moiety of a 3-methyl-1-cyclopentadecene derivative represented by General Formula (II):

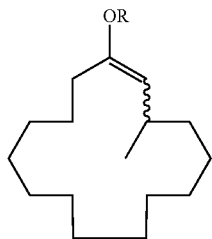
(II)

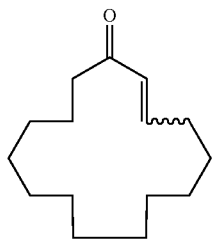
(III)

wherein R represents a straight- or branched-chain acyl group which may have a substituent containing a heteroatom or an aromatic ring, a straight- or branched-chain alkyloxycarbonyl which may have a substituent containing a heteroatom or an aromatic ring, a straight- or branched-chain alkyl group which may have a substituent containing a heteroatom or an aromatic ring; and the wavy line represents a cis isomer and/or a trans isomer of double bond.

4. A method of producing optically active muscone represented by Formula (I-a):

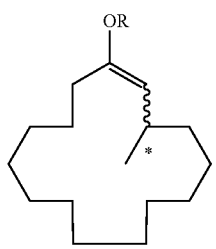
(II-a)

the method comprising solvolyzing an enol moiety of an optically active 3-methyl-1-cyclopentadecene derivative represented by General Formula (II-a):

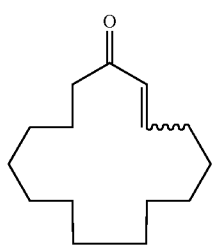
(III)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring; * represents an asymmetric carbon atom; and the wavy line represents a cis isomer and/or a trans isomer of double bond.

5. A method of producing optically active muscone represented by Formula (I-a):

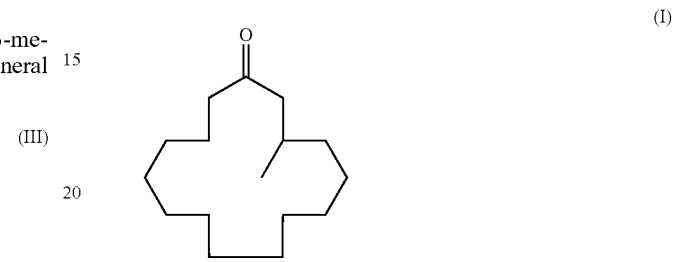
(I)

the method comprising:
reacting 2-cyclopentadecenones represented by General Formula (III):

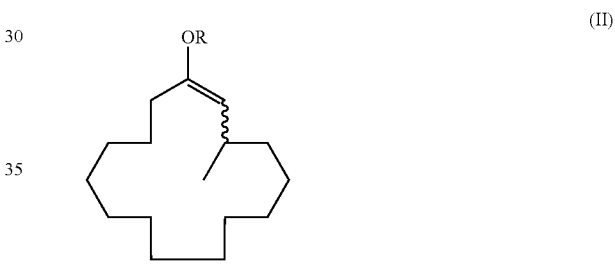
(II)

wherein the wavy line represents a cis isomer and/or a trans isomer of double bond, with an organic metal methylation reagent via 1, 4-conjugation addition reaction in the presence of a copper or nickel catalyst, an enol anion scavenger, and an optically active ligand to give an optically active 3-methyl-1-cyclopentadecene derivative represented by General Formula (II-a):

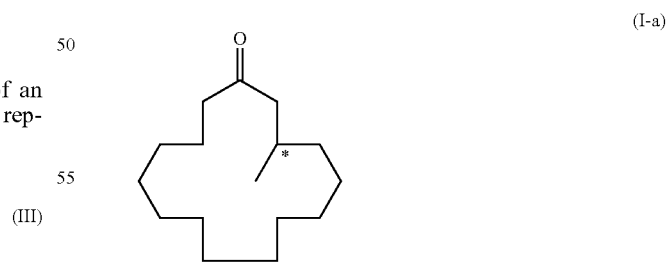
(I-a)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line is the same as that above; and solvolyzing the enol moiety of the optically active 3-methyl-1-cyclopentadecene derivative, wherein the optically active ligand is an optically active ligand represented by General Formula (IV):

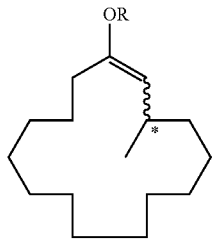

(II-a)

wherein Cn represents a substituted or unsubstituted group having 2 to 4 carbon atoms, which forms a ring together with two oxygen atoms and a phosphorus atom; and $R^1$ and $R^2$ each independently represents a hydrogen atom or a chain or cyclic alkyl, aryl, alkanoyl or aralkyl group that may be substituted with a substituent or $R^1$ and $R^2$ represent groups that can form a heterocyclic ring together with an nitrogen atom connected thereto.

6. A method of producing optically active muscone represented by Formula (I-a):

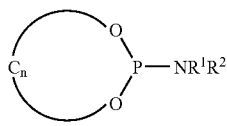

(IV)

the method comprising:
reacting 2-cyclopentadecenones represented by General Formula (III):

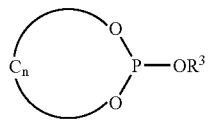

(V)

wherein the wavy line represents a cis isomer and/or a trans isomer of double bond, with an organic metal methylation reagent via 1, 4-conjugation addition reaction in the presence of a copper or nickel catalyst, an enol anion scavenger, and an optically active ligand to give an optically active 3-methyl-1-cyclopentadecene derivative represented by General Formula (II-a):

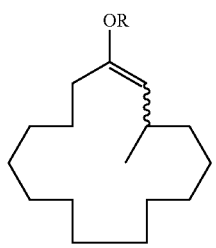

(II)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line is the same as that above; and solvolyzing the enol moiety of the optically active 3-methyl-1-cyclopentadecene derivative, wherein the optically active ligand is an optically active ligand represented by General Formula (V):

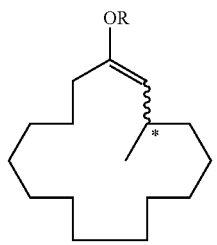

(II-a)

wherein, $C_n$ represents a substituted or unsubstituted group having 2 to 4 carbon atoms, which forms a ring together with two oxygen atoms and a phosphorus atom; and $R^3$ represents a hydrogen atom or a chain or cyclic alkyl, aryl, alkanoyl or aralkyl group that may be substituted with a substituent.

7. A method of producing optically active muscone represented by Formula (I-a):

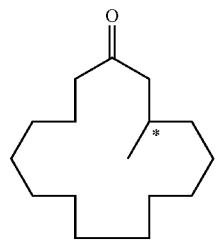

(I-a)

the method comprising:
reacting 2-cyclopentadecenones represented by General Formula (III):

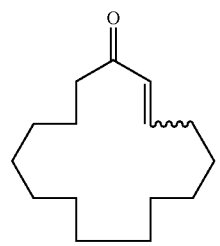

(III)

wherein the wavy line represents a cis isomer and/or a trans isomer of double bond, with an organic metal methylation reagent via 1, 4-conjugation addition reaction in the presence of a copper or nickel catalyst, an enol anion scavenger, and an optically active ligand to give an optically active 3-methyl-1-cyclopentadecene derivative represented by General Formula (II-a)

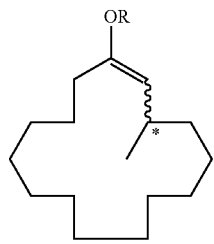

(II-a)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring, or a straight- or branched-chain silyl group which may have a substituent containing a heteroatom or an aromatic ring; * represents an asymmetric carbon atom; and the wavy line is the same as that above; and solvolyzing the enol moiety of the optically active 3-methyl-1-cyclopentadecene derivative, wherein the optically active ligand is 4-(cis-2, 6-dimethylpiperidine)-(R)-ditetrahydronaphthodioxaphosphepin, 4-(cis-2, 6-dimethylpiperidine-(R)-dinaphthodioxaphosphepin, 4-((R, R)-2, 5-diphenylpyrrolidine)-(R)-dinaphthodioxaphosphepin, or 4-((R, R)-2, 5-diphenylpyrrolidine)-(R)-ditetrahydronaphtho-dioxaphosphepin.

8. The production method according to claim 1, 2, 5, or 6, wherein the enol anion scavenger is an enol anion scavenger represented by the following General Formula (VI):

R⁴—X  (VI)

wherein R⁴ represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring; and X represents a halogen atom, an alkylsulfonyloxy group, an arylsulfonyloxy group, or OR', wherein R' represents a straight- or branched-chain acyl group which may have a substituent containing a heteroatom or an aromatic ring, or a straight- or branched-chain alkyloxycarbonyl group which may have a substituent containing a heteroatom or an aromatic ring.

9. The production method according to any of claims 1, 2, 5, or 6, wherein the enol anion scavenger is an enol anion scavenger represented by the following General Formula (VII):

R⁵—X  (VII)

wherein R⁵ represents a straight- or branched-chain acyl group which may have a substituent containing a heteroatom or an aromatic ring, or a straight- or branched-chain alkyloxycarbonyl group which may have a substituent containing a heteroatom or an aromatic ring; and X represents a halogen atom, an alkylsulfonyloxy group, an arylsulfonyloxy group, or OR', wherein R' represents a straight- or branched-chain acyl group which may have a substituent containing a heteroatom or an aromatic ring, or a straight- or branched-chain alkyloxycarbonyl group which may have a substituent containing a heteroatom or an aromatic ring.

10. A 3-methyl-1-cyclopentadecene derivative, represented by General Formula (II):

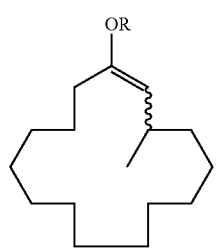

(II)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring; and the wavy line represents a cis isomer and/or a trans isomer of double bond.

11. Optically active 3-methyl-1-cyclopentadecene derivatives, represented by General Formula (II-a):

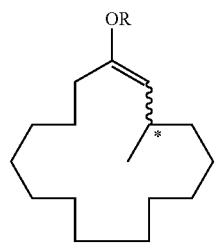

(II-a)

wherein R represents a straight- or branched-chain acyl group which may have a substituent containing a heteroatom or an aromatic ring, a straight- or branched-chain alkyloxycarbonyl group which may have a substituent containing a heteroatom or an aromatic ring, a straight- or branched-chain alkyl group which may have a substituent containing a heteroatom or an aromatic ring; * represents an asymmetric carbon atom; and the wavy line represents a cis isomer and/or a trans isomer of double bond.

* * * * *

UNITED STATES PATENT AND TRADEMARK OFFICE
CERTIFICATE OF CORRECTION

PATENT NO.       : 7,479,574 B2                                    Page 1 of 7
APPLICATION NO.  : 11/667476
DATED            : January 20, 2009
INVENTOR(S)      : Hiroyuki Matsuda et al.

It is certified that error appears in the above-identified patent and that said Letters Patent is hereby corrected as shown below:

IN THE CLAIMS:

In Column 33, Claim 3, first formula from the top, labeled "(II)", change from

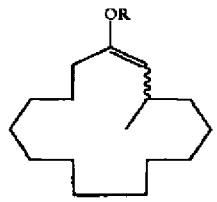
(II)

to the following:

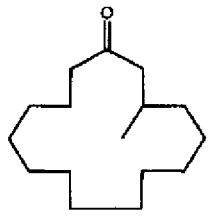
(I)

In Column 33, Claim 3, second formula from the top, labeled "(III)", change from

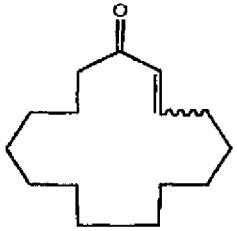
(III)

to the following:

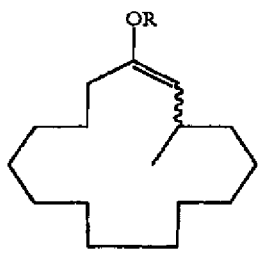
(II)

UNITED STATES PATENT AND TRADEMARK OFFICE
CERTIFICATE OF CORRECTION

PATENT NO.      : 7,479,574 B2                          Page 2 of 7
APPLICATION NO. : 11/667476
DATED           : January 20, 2009
INVENTOR(S)     : Hiroyuki Matsuda et al.

It is certified that error appears in the above-identified patent and that said Letters Patent is hereby corrected as shown below:

In Column 33, Claim 4, third formula from the top, labeled "(II-a)", change from

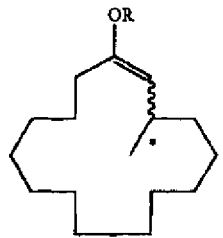
(II-a)

to the following:

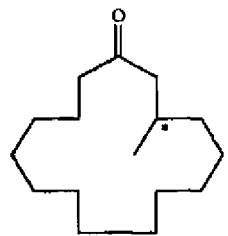
(I-a)

In Column 33, Claim 4, fourth formula from the top, labeled "(III)", change from

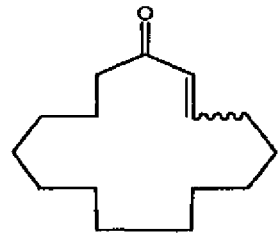
(III)

to the following:

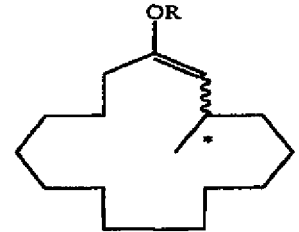
(II-a)

UNITED STATES PATENT AND TRADEMARK OFFICE
CERTIFICATE OF CORRECTION

PATENT NO. : 7,479,574 B2
APPLICATION NO. : 11/667476
DATED : January 20, 2009
INVENTOR(S) : Hiroyuki Matsuda et al.

It is certified that error appears in the above-identified patent and that said Letters Patent is hereby corrected as shown below:

In Column 34, Claim 5, first formula from the top, labeled "(I)", change from:

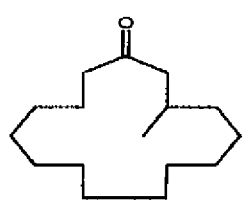

to the following:

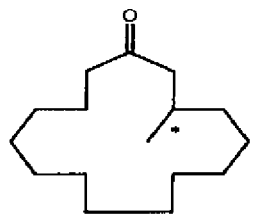

In Column 34, Claim 5, second formula from the top, labeled "(II)", change from:

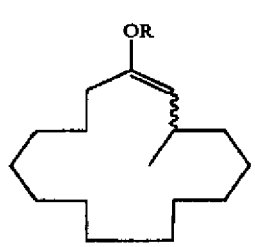

to the following:

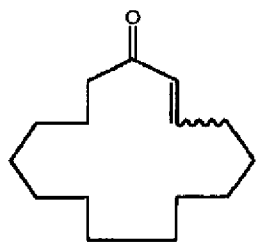

UNITED STATES PATENT AND TRADEMARK OFFICE
CERTIFICATE OF CORRECTION

PATENT NO.        : 7,479,574 B2
APPLICATION NO.   : 11/667476
DATED             : January 20, 2009
INVENTOR(S)       : Hiroyuki Matsuda et al.

It is certified that error appears in the above-identified patent and that said Letters Patent is hereby corrected as shown below:

In Column 34, Claim 5, third formula from the top, labeled "(I-a)", change from:

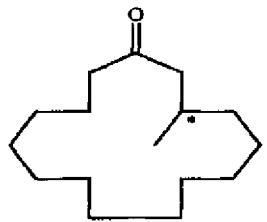

(I-a)

to the following:

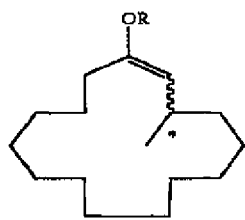

(II-a)

In Column 35, Claim 5, first formula from the top, labeled "(II-a)", change from:

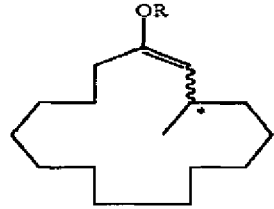

(II-a)

to the following:

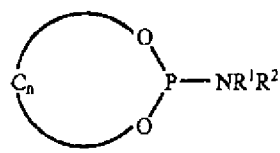

(IV)

UNITED STATES PATENT AND TRADEMARK OFFICE
CERTIFICATE OF CORRECTION

PATENT NO. : 7,479,574 B2  
APPLICATION NO. : 11/667476  
DATED : January 20, 2009  
INVENTOR(S) : Hiroyuki Matsuda et al.

It is certified that error appears in the above-identified patent and that said Letters Patent is hereby corrected as shown below:

In Column 35, Claim 6, second formula from the top, labeled "(IV)", change from:

(IV)

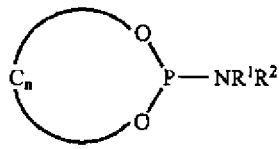

to the following:

(II-a)

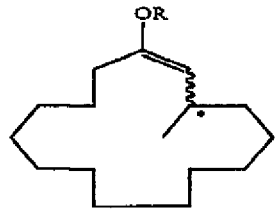

In Column 35, Claim 6, third formula from the top, labeled "(V)", change from:

(V)

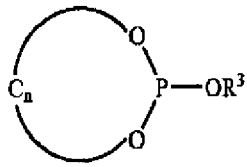

to the following:

(III)

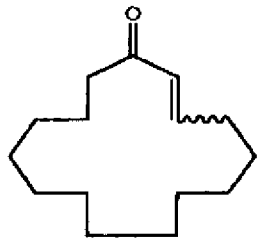

UNITED STATES PATENT AND TRADEMARK OFFICE
CERTIFICATE OF CORRECTION

PATENT NO. : 7,479,574 B2
APPLICATION NO. : 11/667476
DATED : January 20, 2009
INVENTOR(S) : Hiroyuki Matsuda et al.

It is certified that error appears in the above-identified patent and that said Letters Patent is hereby corrected as shown below:

In Column 34, Claim 6, fourth formula from the top, labeled "(II)", change from:

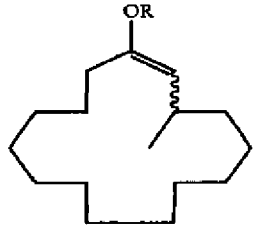

(II)

to the following:

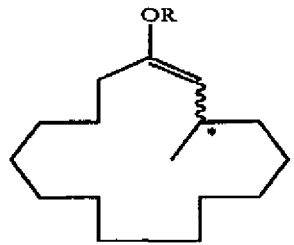

(II-a)

UNITED STATES PATENT AND TRADEMARK OFFICE
CERTIFICATE OF CORRECTION

PATENT NO.       : 7,479,574 B2
APPLICATION NO.  : 11/667476
DATED            : January 20, 2009
INVENTOR(S)      : Hiroyuki Matsuda et al.

It is certified that error appears in the above-identified patent and that said Letters Patent is hereby corrected as shown below:

In Column 36, Claim 6, first formula from the top, labeled "(II-a)", change from:

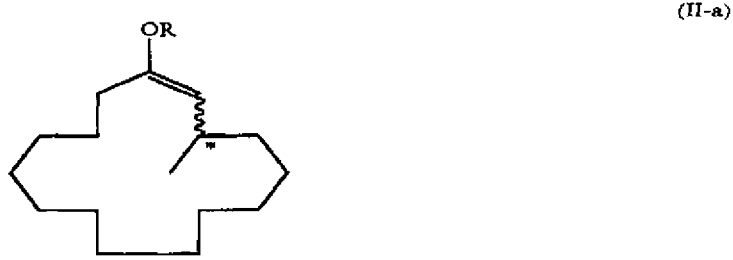

to the following:

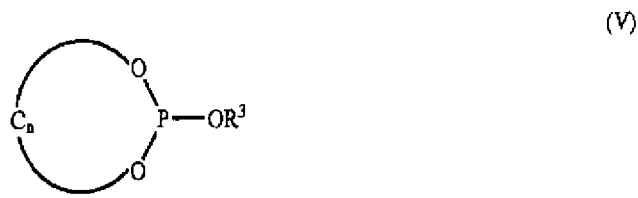

Signed and Sealed this

Twenty-seventh Day of October, 2009

David J. Kappos
*Director of the United States Patent and Trademark Office*